United States Patent
Van Straten et al.

(10) Patent No.: US 8,258,293 B2
(45) Date of Patent: *Sep. 4, 2012

(54) TETRAHYDROQUINOLINE DERIVATIVES

(75) Inventors: Nicole Corine Renee Van Straten, Berghem (NL); Rudolf Gijsbertus Van Someren, Verseveste (NL); Jurgen Schulz, Hamilton (GB)

(73) Assignee: MSD OSS B.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/268,214

(22) Filed: Oct. 7, 2011

(65) Prior Publication Data

US 2012/0202996 A1    Aug. 9, 2012

Related U.S. Application Data

(63) Continuation of application No. 10/482,707, filed as application No. PCT/EP02/07053 on Jun. 25, 2002, now Pat. No. 8,058,441.

(30) Foreign Application Priority Data

Jul. 2, 2001    (EP) ..................... 1202531

(51) Int. Cl.
*C07D 215/08*    (2006.01)
*C07D 215/12*    (2006.01)
*C07D 215/20*    (2006.01)
*C07D 215/38*    (2006.01)
*C07D 215/48*    (2006.01)
*C07D 401/12*    (2006.01)
*C07D 405/12*    (2006.01)
*C07D 405/14*    (2006.01)
*C07D 409/12*    (2006.01)
*C07D 413/12*    (2006.01)
*C07D 417/12*    (2006.01)

(52) U.S. Cl. ........ 544/106; 544/336; 546/152; 546/153; 546/159; 546/161; 546/168; 546/171

(58) Field of Classification Search .......... None
See application file for complete search history.

(56) References Cited

U.S. PATENT DOCUMENTS 8,058,441 B2 * 11/2011 Van Straten et al. .......... 546/152

* cited by examiner

*Primary Examiner* — Janet Andres
*Assistant Examiner* — Timothy R Rozof
(74) *Attorney, Agent, or Firm* — Janet E. Fair; John C. Todaro

(57) ABSTRACT

The present invention relates to tetrahydroquinoline derivatives having general formula I:

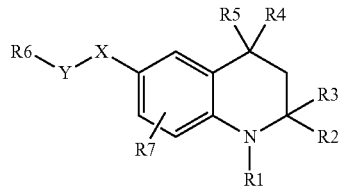

Formula I or a pharmaceutically acceptable salt thereof, wherein R1 is formyl, (1-6C)alkylcarbonyl or (1-6C)alkylsulfonyl; R2 and R3 are H or (1-4C)alkyl; R4 is phenyl; R5 is (1-4C)alkyl; Y—X is C(O)—O, S(O)2-O, NHC(O)—O, NHC(S)—O, OC(O)—O, bond-O, C(O)—NH, S(O)2-NH, NHC(O)—NH, NHC(S)—NH, OC(O)—NH, bond-NH, NH—C(O), O—C(O), NH—S(O)2, or O—S(O)2 or Y—X is a bond; R6 is H, trifluoromethyl, (1-6C) alkyl, 1- or 2-adamantyl(1-4C)alkyl, (2-6C)alkenyl, (2-6C)alkynyl, (3-9C)heteroaryl, (3-6C)cycloalkyl, (2-6C)heterocycloalkyl, (1-4C)alkylthio(1-4C)alkyl, (6-10C)aryl(1-4C)alkyl, (3-9C)heteroaryl(1-4C)alkyl, (3-6C)cycloalkyl(1-4C)alkyl, (2-6C)heterocycloalkyl (1-4C)alkyl, R8,R9-aminocarbonyl(1-4C)alkyl, R8,R9-amino(1-4C)alkyl, R8-oxycarbonyl(1-4C)alkyl, R8-oxy(1-4C)alkyl, R8-carbonyl(1-4C)alkyl or (6-10C) aryl; R7 is H, (1-4C)alkyl, (1-4C)alkoxy, halogen, trifluoromethyl, cyano, nitro, hydroxyl; and R8 and/or R9 is H, (1-4C)alkyl, (2-4C)alkenyl, (2-4C)alkynyl, (6-10C) aryl, (3-9C)heteroaryl, (6-10C)aryl(1-4C)alkyl, (3-9C) heteroaryl(1-4C)alkyl, (3-6C)cycloalkyl(1-4C)alkyl, (2-6C)heterocycloalkyl(1-4C)alkyl, (1-4C)(di)alkylamino(1-4C)alkyl, (1-4C)alkoxy(1-4C)alkyl, (1-4C) alkylthio(1-4C)alkyl, (1-4C)alkylcarbonylamino(1-4C) alkyl, (1-4C)alkoxycarbonyl(1-4C)alkyl, (1-4C) alkoxycarbonylamino(1-4C)alkyl, (3-6C)cycloalkyl, (2-6C)heterocycloalkyl, or R8 and R9 may be joined in a (2-6C)heterocycloalkyl ring.

The present invention also relates to pharmaceutical compositions comprising said derivatives and the use of these derivatives to control fertility.

3 Claims, No Drawings

TETRAHYDROQUINOLINE DERIVATIVES

CROSS REFERENCE TO RELATED APPLICATIONS

This application is a continuation application of application Ser. No. 10/482,707, filed Jan. 2, 2004, which is a national stage application under 35 U.S.C. 371 of International Patent Application No.: PCT/EP2002/07053, filed Jun. 25, 2002. which claims the benefit of European Application 01202531.8, filed Jul. 2, 2001. Each of the aforementioned applications is incorporated by reference in its entirety as if fully set forth herein.

The invention relates to a compound having FSH modulatory activity, in particular a tetrahydroquinoline derivative, to a pharmaceutical composition containing the same, as well as the use of said compound in medical therapy.

Gonadotropins serve important functions in a variety of bodily functions including metabolism, temperature regulation and the reproductive process. Gonadotropins act on specific gonadal cell types to initiate ovarian and testicular differentiation and steroidogenesis. The hypophyseal gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787-807, 1990; Dorrington and Armstrong, Recent Prog. Horm. Res. 35:301-342, 1979). Currently, FSH is applied clinically, in combination with LH, for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and oestrogens, and from the placenta during pregnancy. In the female, FSH acts on the ovaries promoting development of follicles and is the major hormone regulating secretion of oestrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. Recombinant human FSH is available commercially and is being used in assisted reproduction (Olijve et al. Mol. Hum. Reprod. 2:371, 1996; Devroey et al. Lancet 339:1170, 1992).

The actions of the FSH hormone are mediated by a specific plasma membrane receptor that is a member of the large family of G-protein coupled receptors. These receptors consist of a single polypeptide with seven transmembrane domains and are able to interact with the Gs protein, leading to the activation of adenylate cyclase.

The FSH receptor is a highly specific target in the ovarian follicle growth process and is exclusively expressed in the ovary. Blocking this receptor or inhibiting the signaling which is normally induced after FSH-mediated receptor activation will disturb follicle development and thus ovulation and fertility. Low molecular weight FSH antagonists could therefore form the basis for new contraceptives. Such FSH antagonists could give rise to diminished follicle development (no ovulation) with still sufficient estrogen production left to avoid adverse effects on e.g. bone mass.

The present invention describes the preparation of low molecular weight hormone analogs that selectively have modulatory activity on the FSH receptor. The compounds of the invention can either be used as (partial) agonists or (partial) antagonists of the FSH-receptor.

Thus, it has now been found, that the following class of tetrahydroquinoline compounds of formula I or pharmaceutically acceptable salts thereof, have FSH-modulatory activity:

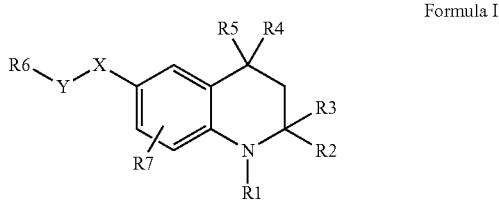

Formula I wherein
$R^1$ is formyl, (1-6C)alkylcarbonyl or (1-6C)alkylsulfonyl;
$R^2$ and $R^3$ are H or (1-4C)alkyl;
$R^4$ is phenyl, optionally substituted with one or more substituents selected from the group hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino. Preferable position of substitution is the para-position.
$R^5$ is (1-4C)alkyl;
Y—X is C(O)—O, S(O)$_2$—O, NHC(O)—O, NHC(S)—O, OC(O)—O, bond-O, C(O)—NH, S(O)$_2$—NH, NHC(O)—NH, NHC(S)—NH, OC(O)—NH, bond-NH, NH—C(O), O—C(O), NH—S(O)$_2$, or O—S(O)$_2$ or X—Y is a bond;
$R^6$ is H, trifluoromethyl, (1-6C)alkyl, 1- or 2-adamantyl(1-4C)alkyl, (2-6C)alkenyl, (2-6C)alkynyl, (6-10C)aryl, (3-9C)heteroaryl, (3-6C)cycloalkyl, (2-6C)heterocycloalkyl, (1-4C)alkylthio(1-4C)alkyl, (6-10C)aryl(1-4C)alkyl, (3-9C)heteroaryl(1-4C)alkyl, (3-6C)cycloalkyl(1-4C)alkyl, (2-6C)heterocycloalkyl(1-4C)alkyl, $R^8,R^9$-aminocarbonyl(1-4C)alkyl, $R^8,R^9$-amino(1-4C)alkyl, $R^8$-oxycarbonyl(1-4C)alkyl, $R^8$-oxy(1-4C)alkyl, $R^8$-carbonyl(1-4C)alkyl;

If $R^6$ is H, it is to be noted that X—Y may not be a bond.

If $R^6$ is phenyl, phenyl may, in addition to the substituents for (6-10C)aryl groups as mentioned in the definitions, optionally be substituted with (6-10C)aryl, (6-10C)aryloxy, (6-10C)aryl(1-4C)alkoxy, (3-9C)heteroaryl, (3-9C)heteroaryloxy, (3-9C)heteroaryl(1-4C)alkoxy, (1-4C)alkylcarbonylamino, (1-4C)alkylcarbonyloxy, (3-6C)cycloalkylcarbonyloxy, (1-4C)alkoxycarbonyl(1-4C)alkylcarbonyloxy, (1-4C)alkoxy(1-4C)alkylcarbonyloxy, (6-10C)arylcarbonyloxy, (3-9C)heteroarylcarbonyloxy, (1-4C)alkylsulfonyloxy, (6-10C)arylsulfonyloxy, (3-9C)heteroarylsulfonyloxy, (1-4C)(di)alkylcarbamoyl, (6-10C)(di)arylcarbamoyl, (2-6C)heterocycloalkylcarbamoyl, (6-10C)(di)arylamino, (3-6C)cycloalkyl, (3-6C)cycloalkyl(1-4C)alkyl, (2-6C)heterocycloalkyl, (2-6)heterocycloalkyl(1-4C)alkyl.

$R^7$ is H, (1-4C)alkyl, (1-4C)alkoxy, halogen, trifluoromethyl, cyano, nitro, hydroxyl; $R^8$ and/or $R^9$ is H, (1-4C)alkyl, (2-4C)alkenyl, (2-4C)alkynyl, (6-10C)aryl, (3-9C)heteroaryl, (6-10C)aryl(1-4C) (3-9C)heteroaryl(1-4C)alkyl, (3-6C)cycloalkyl(1-4C)alkyl, (2-6C)heterocycloalkyl(1-4C) alkyl, (1-4C)(di)alkylamino(1-4C)alkyl, (1-4C)alkoxy(1-4C)alkyl, (1-4C)alkylthio(1-4C)alkyl, (1-4C)alkylcarbonylamino(1-4C)alkyl, (1-4C)alkoxycarbonyl(1-4C)alkyl, (1-4C)alkoxycarbonylamino(1-4C)alkyl, (3-6C)cycloalkyl, (2-6C)heterocycloalkyl, or $R^8$ and $R^9$ may be joined in a (2-6C)heterocycloalkyl ring.

The compounds according to the present invention modulate the FSH receptor function and can be used for the same clinical purposes as native FSH if they behave like agonists, with the advantage that they display altered stability properties and may be administered differently. If they block the FSH receptor they can be used e.g. as a contraceptive agent.

Thus, the FSH-receptor modulators of the present invention may be used for treating infertility, for contraception and for treatment of hormone-dependent disorders such as breast cancer, prostate cancer, and endometriosis. Preferably the compounds of the present invention are used to inactivate the FSH-receptor.

The term (1-4C)alkyl as used in the definition means a branched or unbranched alkyl group having 1-4 carbon atoms, for example methyl, ethyl, propyl, isopropyl, butyl, sec-butyl and tert-butyl.

The term (1-6C)alkyl as used in the definition means a branched or unbranched alkyl group having 1-6 carbon atoms, for example methyl, ethyl, propyl, isopropyl, butyl, sec-butyl, tert-butyl and hexyl. (1-5C)Alkyl groups are preferred, (1-4C)alkyl being the most preferred.

The term 1- or 2-adamantyl(1-4C)alkyl means an adamantyl group attached at position 1 or 2 to an alkyl group containing 1-4 carbon atoms, with the same meaning as previously defined.

The term (2-4C)alkenyl means a branched or unbranched alkenyl group having 2-4 carbon atoms, such as ethenyl and 2-butenyl.

The term (2-6C)alkenyl means a branched or unbranched alkenyl group having 2-6 carbon atoms, such as ethenyl, 2-butenyl, and n-pentenyl.

The term (2-4C)alkynyl means a branched or unbranched alkynyl group having 2-4 carbon atoms, such as ethynyl and propynyl.

The term (2-6C)alkynyl means a branched or unbranched alkynyl group having 2-6 carbon atoms, such as ethynyl, propynyl and n-pentynyl.

The term (3-6C)cycloalkyl means a cycloalkyl group having 3-6 carbon atoms, being cyclopropyl, cyclobutyl, cyclopentyl and cyclohexyl.

The term (2-6C)heterocycloalkyl means a heterocycloalkyl group having 2-6 carbon atoms, preferably 3-5 carbon atoms, and at least including one heteroatom selected from N, O and/or S, which may be attached via a heteroatom if feasible, or a carbon atom. Preferred heteroatoms are N or O. Most preferred are piperidine, morpholine and pyrrolidine.

The term (1-4C)alkoxy means an alkoxy group having 1-4 carbon atoms, the alkyl moiety having the same meaning as previously defined. (1-2C)Alkoxy groups are preferred.

The term (6-10C)aryl means an aromatic hydrocarbon group having 6-10 carbon atoms, such as phenyl, naphthyl, tetrahydronaphthyl or indenyl, which may optionally be substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino, the alkyl moieties having the same meaning as previously defined. The preferred aromatic hydrocarbon group is phenyl.

The term (3-9C)heteroaryl means a substituted or unsubstituted aromatic group having 3-9 carbon atoms, at least including one heteroatom selected from N, O and/or S, like imidazolyl, thiadiazolyl, pyridyl, (benz)thienyl, (benzo)furyl, quinolyl, tetrahydroquinolyl, quinoxalyl or indolyl. The substituents on the heteroaryl group may be selected from the group of substituents listed for the aryl group. The heteroaryl group may be attached via a carbon atom or a heteroatom, if feasible. Preferred heteroaryl groups are thienyl, furyl and pyridyl.

The term (6-10C)aryloxy means an aryl group containing 6-10 carbon atoms as defined previously, attached to an oxygen atom. (3-9C)Heteroaryloxy groups are analogs of the (6-10C)aryloxy groups, at least including one heteroatom selected from N, O or S.

The term (1-4C)alkoxycarbonyl(1-4C)alkyl means an alkoxycarbonylalkyl group, wherein the alkoxy group contains 1-4 carbon atoms with the same meaning as previously defined and the alkyl group contains 1-4 carbon atoms with the same meaning as previously defined.

The term (1-4C)alkoxy(1-4C)alkyl means an alkoxyalkyl group, wherein the alkoxy group contains 1-4 carbon atoms with the same meaning as previously defined and the alkyl group contains 1-4 carbon atoms with the same meaning as previously defined.

The term (3-6C)cycloalkyl(1-4C)alkyl means a cycloalkyl group of 3-6 carbon atoms attached to an alkyl group of 1-4 carbon atoms, wherein the cycloalkyl group is a (3-6C)cycloalkyl group as previously defined and the alkyl group is a (1-4C)alkyl group as previously defined.

The term (2-6C)heterocycloalkyl(1-4C)alkyl means a heterocycloalkyl group of 2-6 carbon atoms attached to an alkyl group of 1-4 carbon atoms, wherein the heterocycloalkyl group is a (2-6C)heterocycloalkyl group as previously defined and the alkyl group is a (1-4C)alkyl group as previously defined.

The term (1-4C)(di)alkylamino means a (di)alkylamino group, the alkyl groups of which contain 1-4 carbon atoms and have the same meaning as previously defined.

The term (6-10C)(di)arylamino means a (di)arylamino group, the aryl groups of which contain 6-10 carbon atoms and have the same meaning as previously defined.

The term (1-4C)(di)alkylamino(1-4C)alkyl means a (di)alkylaminoalkyl group, the alkyl groups of which contain 1-4 carbon atoms and have the same meaning as previously defined.

The term (1-4C)alkylthio(1-4C)alkyl means an alkylthioalkyl group, the alkyl groups of which contain 1 to 4 carbon atoms and have the same meaning as defined previously.

The term aminocarbonyl(1-4C)alkyl in the definition of $R^8,R^9$-aminocarbonyl(1-4C)alkyl means an aminocarbonylalkyl group, the alkyl group of which contains 1-4 carbon atoms and has the same meaning as previously defined. The aminocarbonylmethyl group is the preferred aminocarbonylalkyl group.

The term amino(1-4C)alkyl in the definition of $R^8,R^9$-amino(1-4C)alkyl means an aminoalkyl group, the alkyl group of which contains 1-4 carbon atoms and has the same meaning as previously defined.

The term oxycarbonyl(1-4C)alkyl in the definition of $R^8$-oxycarbonyl(1-4C)alkyl means an oxycarbonylalkyl group, the alkyl group of which contains 1-4 carbon atoms and has the same meaning as previously defined. The oxycarbonylmethyl group is the preferred oxycarbonylalkyl group.

The term oxy(1-4C)alkyl in the definition of $R^8$-oxy(1-4C)alkyl means an oxyalkyl group, the alkyl group of which contains 1-4 carbon atoms and has the same meaning as previously defined.

The term carbonyl(1-4C)alkyl in the definition of $R^8$-carbonyl(1-4C)alkyl means a carbonylalkyl group, the alkyl group of which contains 1-4 carbon atoms and has the same meaning as previously defined.

The term (6-10C)aryl(1-4C)alkyl means an arylalkyl group having 7-14 carbon atoms, wherein the alkyl group is a (1-4C)alkyl group and the aryl group is a (6-10C)aryl as previously defined. Phenyl(1-4C)alkyl groups are preferred arylalkyl groups, such as benzyl. (3-9C)Heteroaryl(1-4C) alkyl groups are analogs of the (6-10C)aryl(1-4C)alkyl groups, at least including one heteroatom selected from N, O and/or S, the heteroaryl group of which may be attached via a carbon atom or via a heteroatom if feasible.

The term joined in a (2-6C)heterocycloalkyl ring in the definition of NR$^8$R$^9$, where R$^8$ and R$^9$ together with the nitrogen atom to which they are attached form a ring, means a ring containing the nitrogen atom and further having at most 2-6 carbon atoms, which ring may contain one or more additional heteroatoms selected from N, O and/or S. Examples of such rings are azetidine, pyrrolidine, piperidine, piperazine, and (thio)morpholine.

The term halogen means fluorine, chlorine, bromine or iodine.

The term (1-6C)alkylcarbonyl means an alkylcarbonyl group, the alkyl group of which contains 1-6 carbon atoms and has the same meaning as previously defined. (1-4C)Alkylcarbonyl groups are preferred.

The term (1-4C)alkylcarbonylamino(1-4C)alkyl means an alkylcarbonylaminoalkyl group, the alkyl groups of which contain 1-4 carbon atoms and have the same meaning as previously defined.

The term (6-10C)aryl(1-4C)alkoxy means an aryl group containing 6-10 carbon atoms as defined previously, attached to an (1-4C)alkoxy group as defined previously. (3-9C)Heteroaryl(1-4C)alkoxy groups are analogs of the (6-10C)aryl (1-4C)alkoxy groups, at least including one heteroatom selected from N, O or S, the heteroaryl group of which may be attached via a carbon atom or via a heteroatom, if feasible.

The term (1-4C)alkylcarbonyloxy means an alkylcarbonyloxy group the alkyl group of which contains 1-4 carbon atoms. The term (3-6C)cycloalkylcarbonyloxy means a cycloalkylcarbonyloxy group the cycloalkyl group of which contains 3-6 carbon atoms, the cycloalkyl moiety of which has the same meaning as previously defined.

The term (1-4C)alkoxycarbonyl(1-4C)alkylcarbonyloxy means an (1-4C)alkoxycarbonyl group attached to an alkylcarbonyloxy group the alkyl moiety of which contains 1-4 carbon atoms, the alkoxy group of which has the same meaning as previously defined.

The term (1-4C)alkoxy(1-4C)alkylcarbonyloxy means an alkoxy group with 1-4 carbon atoms attached to an alkylcarbonyloxy group with 1-4 carbon atoms, the alkoxy and alkyl groups having the same meaning as previously defined.

The term (1-4C)alkylcarbonylamino means an alkylcarbonylamino group the alkyl group of which contains 1-4 carbon atoms.

The term (1-4C)alkoxycarbonylamino(1-4C)alkyl means an alkoxycarbonyl group containing 1-4 carbon atoms with the same meaning as previously defined, attached to an aminoalkyl group, the alkyl group of which contains 1-4 carbon atoms with the same meaning as previously defined.

The term (6-10C)arylcarbonyloxy means an arylcarbonyloxy group the aryl group of which contains 6-10 carbon atoms. Preferred arylcarbonyloxy group is a phenylcarbonyloxy group. (3-9C)Heteroarylcarbonyloxy groups are analogs of the (6-10C)arylcarbonyloxy groups, at least including one heteroatom selected from N, O or S and may be attached via a carbon atom or a heteroatom, if feasible.

The term (1-4C)alkylsulfonyl means an alkylsulfonyl group, the alkyl group of which contains 1-4 carbon atoms and has the same meaning as previously defined.

The term (1-6C)alkylsulfonyl means an alkylsulfonyl group, the alkyl group of which contains 1-6 carbon atoms and has the same meaning as previously defined. (1-3C) Alkylsulfonyl groups are preferred.

The term (1-4C)alkylsulfonyloxy means an alkylsulfonyloxy group, the alkyl group of which contains 1-4 carbon atoms and has the same meaning as previously defined. (1-3C)Alkylsulfonyloxy groups are preferred.

The term (6-10C)arylsulfonyloxy means an arylsulfonyloxy group, the aryl group of which contains 6-10 carbon atoms and has the same meaning as previously defined. The phenylsulfonyloxy group is preferred. (3-9C)Heteroarylsulfonyloxy groups are analogs of the (6-10C)arylsulfonyloxy groups, at least including one heteroatom selected from N, O or S, which may be attached via a carbon atom or a heteroatom, if feasible.

The term (1-4C)(di)alkylcarbamoyl means a (di)alkylcarbamoyl group, the alkyl groups of which contain 1-4 carbon atoms and have the same meaning as previously defined.

The term (6-10C)(di)arylcarbamoyl means a (di)arylcarbamoyl group, the aryl moieties of which contains 6-10 carbon atoms and have the same meaning as previously is defined.

The term (2-6C)heterocycloalkylcarbamoyl means a heterocycloalkylcarbamoyl group, the heterocycloalkyl group of which contains 2-6 carbon atoms and has the same meaning as previously defined.

Preferred compounds of the invention are compounds of formula I, wherein Y—X is C(O)—NH, OC(O)—NH, or C(O)—O. More preferred are compounds wherein Y—X is C(O)—NH.

Further preferred are compounds wherein. R$^1$ is (1-4C) alkylcarbonyl, preferably acetyl and/or R$^2$ and/or R$^3$ and R$^5$ are independently (1-4C)alkyl, more preferably methyl.

R$^6$ preferably is a bulky group. Preferred compounds are those wherein R$^6$ is (6-10C)aryl, (3-9C)heteroaryl, (6-10C) aryl(1-4C)alkyl or (3-9C)heteroaryl(1-4C)alkyl. Most preferred are compounds wherein R$^6$ is (6-10C)aryl, even more preferred phenyl. The preferred R$^7$ group is H, (1-4C)alkyl or (1-4C)alkoxy. Most preferred are H or (1-4C)alkyl, even more preferred H or methyl. Most preferred are compounds wherein R$^7$ is H.

In the most preferred compounds according to the invention R$^1$ is (1-4C)alkylcarbonyl, R$^2$, R$^3$, R$^5$ are independently (1-4C)alkyl, R$^4$ is phenyl and Y—X is C(O)—NH and R$^7$ is H. Even more preferred are compounds wherein R$^1$ is acetyl, R$^2$, R$^3$, R$^5$ are independently methyl, R$^4$ is phenyl and Y—X is C(O)—NH and R$^7$ is H.

In the above-mentioned preferred compounds substitutions are allowed as indicated in the definitions of the groups. Phenyl in R$^6$ can in addition be substituted as indicated in the definition for R$^6$.

Excluded from the invention are the compounds I-acetyl-6-benzoylamino-4-(4-methylphenyl)-1,2,3,4-tetrahydro-2,2,4-trimethylquinoline, 1-acetyl-4-phenyl-1,2,3,4-tetrahydro-2,2,4,6-tetramethylquinoline, 1-acetyl-4-phenyl-1,2,3,4-tetrahydro-2,2,4,6,8-pentamethylquinoline, 1-acetyl-6-methoxy-4-phenyl-1,2,3,4-tetrahydro-2,2,4-trimethylquinoline, 1-acetyl-6-trifluoroacetylamino-4-(4-methylphenyl)-1,2,3,4-tetrahydro-2,2,4-trimethylquinoline, 1-acetyl-6-trifluoroacetylamino-4-phenyl-1,2,3,4-tetrahydro-2,2,4-trimethylquinoline, 1-acetyl-4-(4-chlorophenyl)-1,2,3,4-tetrahydro-2,2,4,6-tetramethylquinoline and 1-acetyl-4-(4-bromophenyl)-1,2,3,4-tetrahydro-2,2,4,6-tetramethylquinoline.

The disclaimer relates to the disclosures in Ref. Zh., Khim. Abstr. No. 1Zh311, 1972; Khim. Geterosikl. Soedin. 7:795, 1971; Ambinter Screening Collection, order nrs 28020-A0839/0039328 (CAS 310456-97-4) and -A0705/0032919

(CAS 327981-38-4); ChemDiv. Inc. order nr 8005-9747 (CAS360760-14-1); ChemStar Product list, order nr CHS0065413 (CAS 299418-67-0); Asinex Compound Collection, order nr BAS0068990 (CAS 299970-20-0).

Suitable methods for the preparation of the compounds of the invention are outlined below.

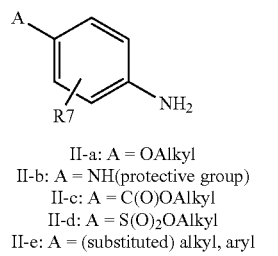

II-a: A = OAlkyl
II-b: A = NH(protective group)
II-c: A = C(O)OAlkyl
II-d: A = S(O)$_2$OAlkyl
II-e: A = (substituted) alkyl, aryl

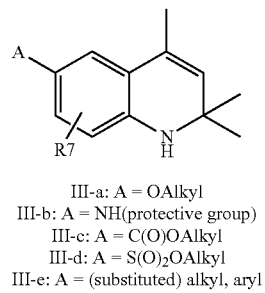

III-a: A = OAlkyl
III-b: A = NH(protective group)
III-c: A = C(O)OAlkyl
III-d: A = S(O)$_2$OAlkyl
III-e: A = (substituted) alkyl, aryl The compounds of the present invention in which $R^2$ and $R^3$ are methyl can be prepared starting from (protected) anilines of general formula II-a-e in which $R^7$ has the same meaning as previously defined, by means of the well-documented Skraup reaction, which yields 1,2-dihydro-2,2,4-trimethylquinoline derivatives of formula III-a-e.

Related Skraup cyclizations are found in literature: A. Knoevenagel, Chem. Ber. 54:1726, 1921; R. L. Atkins and D. E. Bliss, J. Org. Chem. 43:1975, 1978; J. V. Johnson, B. S. Rauckman, D. P. Baccanari and B. Roth, J. Med. Chem. 32:1942, 1989; W. C. Lin, S.-T. Huang and S.-T. Lin, J. Chin. Chem. Soc. 43:497, 1996; J. P. Edwards, S. J. West, K. B. Marschke, D. E. Mais, M. M. Gottardis and T. K. Jones, J. Med. Chem. 41:303, 1998.

The abovementioned reaction is typically conducted at elevated temperature in acetone, mesityl oxide or ethylacetoacetate in the presence of iodine or protic acid such as hydrochloric acid, p-toluenesulfonic acid or aqueous hydrogen iodide. Alternatively, 1,2-dihydro-2,2,4-trimethylquinolines of formula III-a-e can be prepared by reacting the corresponding aniline of formula II-a-e with acetone in the presence of MgSO$_4$, 4-tert-butylcatechol and iodine (L. G. Hamann, R. I. Higuchi, L. Zhi, J. P. Edwards and X.-N. Wang, J. Med. Chem, 41:623, 1998). Starting materials can be either obtained directly from commercial sources or prepared by art-known aromatic ring substitutions, as are described e.g. by H. Cerfontain, Y. Zou and B. H. Bakker, Recl. Tray. Chim. Pays-Bas, 113:403, 1994; A. Coppock, J. Org. Chem. 22:325, 1957; M. Schlosser, J. H. Choi and S. Takagishi, Tetrahedron, 46:5633, 1990.

Alternatively, compounds of general structure VI-a-e, in which $R^2$ and $R^3$ are (2-4C)alkyl and $R^7$ is as previously defined, can generally be synthesized by cyclization of an aniline of formula IV-a-e with an appropriate ketone of formula V.

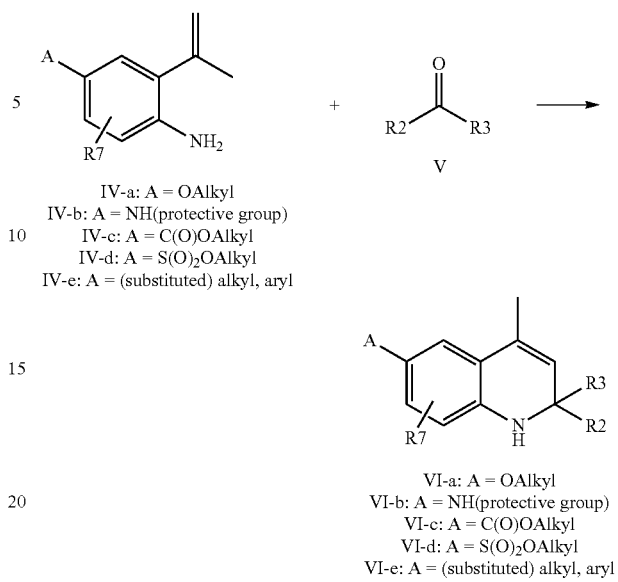

IV-a: A = OAlkyl
IV-b: A = NH(protective group)
IV-c: A = C(O)OAlkyl
IV-d: A = S(O)$_2$OAlkyl
IV-e: A = (substituted) alkyl, aryl VI-a: A = OAlkyl
VI-b: A = NH(protective group)
VI-c: A = C(O)OAlkyl
VI-d: A = S(O)$_2$OAlkyl
VI-e: A = (substituted) alkyl, aryl The abovementioned reaction is typically conducted in an inert solvent such as toluene, at elevated temperature using protic or Lewis acids such as, but not limited to, p-toluenesulfonic acid or borontrifluoride to promote the cyclization (H. Walter, H. Sauter and T. Winkler, Helv. Chim. Acta, 75:1274, 1992; H. Walter, Helv. Chim. Acta, 77; 608, 1994; H. Walter and J. Schneider, Heterocycles, 41:1251, 1995; J. P. Edwards, J. D. Ringgenberg and T. K. Jones, Tetrahedron Lett. 39:5139, 1998).

The requisite building blocks of formula IV-a-e may be prepared by Wittig reaction of ketones of formula VII-a-e. Introduction of substituents A on the aromatic ring can be accomplished using art-known aromatic ring substitutions either in the aniline stage or in the 1,2-dihydro-2,2,4-trimethylquinoline stage, as was mentioned above for compounds of formula II.

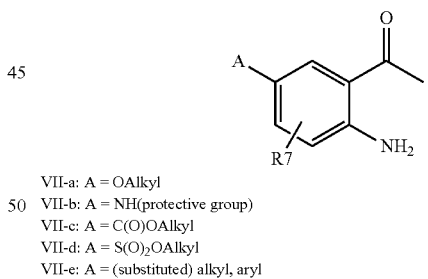

VII-a: A = OAlkyl
VII-b: A = NH(protective group)
VII-c: A = C(O)OAlkyl
VII-d: A = S(O)$_2$OAlkyl
VII-e: A = (substituted) alkyl, aryl In another approach, compounds of formula VI-a-e in which $R^2$=$R^3$=H can be prepared from anilines of general formula II-a-e by reaction with 1-methylstyrene and formaldehyde in acetonitrile at ambient or elevated temperature. Related cyclizations are described in literature: J. M. Mellor and G. D. Merriman, Tetrahedron, 51:6115, 1995.

Subsequent 1-N-acylation or 1-N-sulfonylation of compounds of formula VI wherein $R^2$, $R^3$, $R^7$ and A are as previously defined, can be carried out using standard conditions, well known to those skilled in the art. In a typical experiment, compounds of formula VI are reacted in a solvent such as dichloromethane, tetrahydrofuran, toluene or pyridine with an acylhalide or acid anhydride or a sulfonylchloride in the presence of a base such as, but not limited to, N,N-diisopropylethylamine, triethylamine, piperidine or sodium hydride to give N-acylated or N-sulfonylated 1,2-dihydro-4-methylquinoline derivatives of formula VIII-a and VIII-b, respectively.

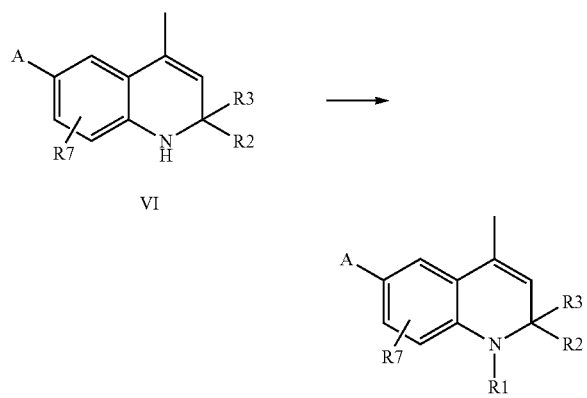

VI

VIII-a: $R^1$ = C(O)Alkyl
VIII-b: $R^1$ = S(O)$_2$Alkyl

Related N-acylations of a dihydroquinoline scaffold are found in literature: Zh. V. Shmyreva, Kin. S. Shikhaliev and E. B. Shpanig, Izv. Vyssh. Uchebn. Zaved., Khim. Khim. Tekhnol. 31:45, 1988; Zh. V. Shmyreva, Kh. S. Shikhaliev, L. P. Zalukaev, Y. A. Ivanov, Y. S. Ryabokobylko and I. E. Pokrovskaya, Zh. Obshch. Khim. 59:1391, 1989.

1-N-Formylation can be readily established by reaction of dihydroquinoline of formula VI with formic acid in the presence of trifluoroacetic acid at elevated temperature (see for example P. Bouyssou, C. Le Goff and J. Chenault, J. Heterocycl. Chem. 29:895, 1992) or with formic acid ethyl ester in the presence of sodium acetate, as was described in literature by e.g. N. Atanes, S. Perez, E. Guitan, L. Castedo and J. M. Saa, Tetrahedron, 50:11257, 1994.

Introduction of the requisite phenyl group at position 4 of the dihydroquinoline scaffold can be accomplished via Friedel-Crafts alkylation of (substituted) benzene derivatives with the compounds of general structure VIII, wherein $R^1$, $R^2$, $R^3$, $R^7$ and A are as previously defined.

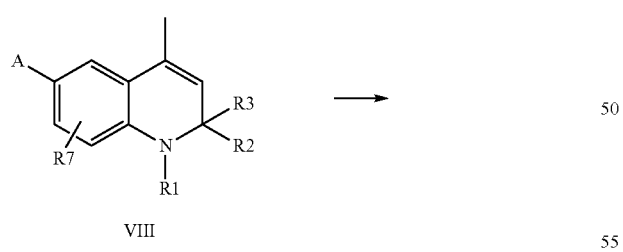

VIII

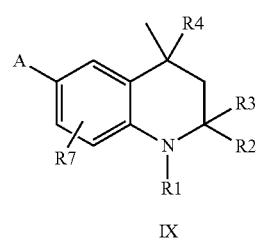

IX

The latter reaction is typically conducted at elevated temperatures either in neat (substituted) benzene or in an appropriate inert solvent such as heptane or hexane with (substituted) benzene as reagent, under catalysis of a Lewis acid (e.g. AlCl$_3$, AlBr$_3$, FeCl$_3$ or SnCl$_4$). Friedel-Crafts alkylation with 1,2-dihydro-2,2,4-trimethylquinolines are described in literature by B. A. Lugovik, L. G. Yudin and A. N. Kost, Dokl. Akad. Nauk SSSR, 170:340, 1966; B. A. Lugovik, L. G. Yudin, S. M. Vinogradova and A. N. Kost, Khim. Geterosikl. Soedin, 7:795, 1971.

Compounds of the present invention, wherein $R^5 \neq Me$ and $R^1$, $R^2$, $R^3$, $R^4$, $R^7$ and A are as previously defined, represented by formula XII, may be synthesized starting from tetrahydroquinoline ketones of formula X. Thus, Wittig reaction of a ketone of formula X with the appropriate Wittig reagent yields the unsaturated derivative represented by formula XI, which in turn is the starting material for a Friedel-Crafts alkylation of (substituted) benzene, via the same procedure as was outlined above for the preparation of compounds with general structure IX.

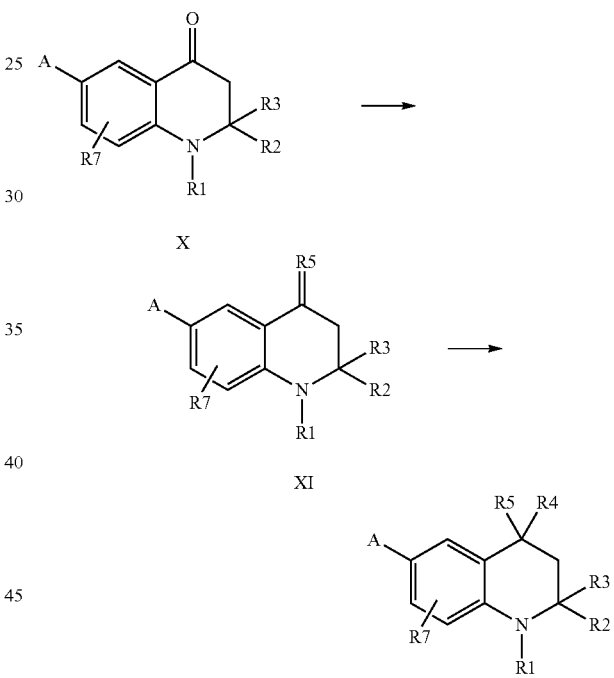

X

XI

XII

The abovementioned Wittig reaction is well known to those skilled in the art.

The requisite ketone of formula X can be prepared by reaction of an aniline of formula II with 3-chloro-3-methyl-1-butyne (XIII) in diethylether/water in the presence of copper powder and triethylamine which yields an alkyne of formula XIV. Hydrogen-halogen exchange can be carried out by deprotonation of a compound of formula XIV in an inert solvent such as tetrahydrofuran with n-butyllithium at temperatures below −50° C. upon addition of p-toluenesulfonylchloride to give a chloride of general formula XV. Finally, acid-catalyzed (e.g. sulfuric acid) cyclization can be carried out at elevated temperature in a solvent such as polyethyleneglycol to give compounds of formula XVI, which can be acylated or sulfonylated as was previously described for derivatives of general formula VI.

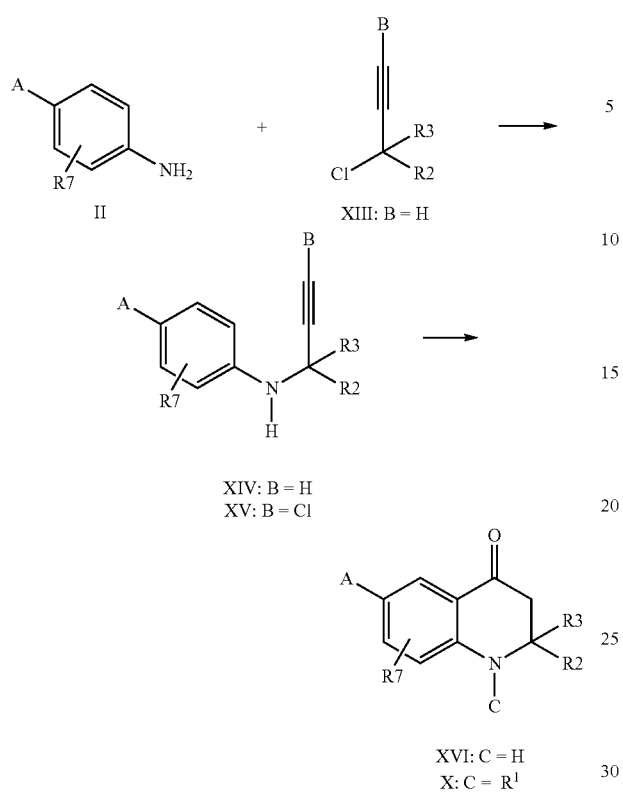

XIII: B = H

XIV: B = H
XV: B = Cl

XVI: C = H
X: C = R¹

The abovementioned reaction sequence is described in literature: P. Barmettler and H.-J. Hansen, Helv. Chim. Acta, 73:1515, 1990 (and references cited in there).

Functionalization of position 6 in tetrahydroquinolines of general structure XII can be accomplished via art-known deprotection-coupling procedures:

Compounds of the present invention wherein X=O and Y=C(O), S(O)$_2$, NHC(O), NHC(S), OC(O) or a bond, represented by formula I-a, can be prepared from 6-methoxy-containing tetrahydroquinoline of formula XII-a. Demethylation is well known to those skilled in the art.

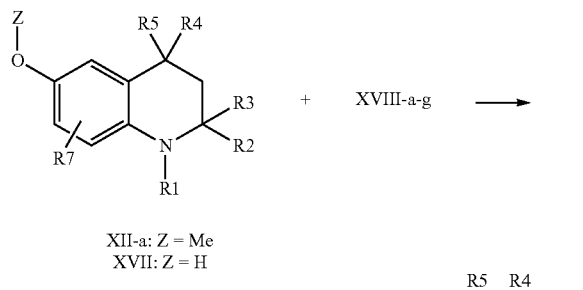

XII-a: Z = Me
XVII: Z = H

I-a

In a typical experiment, demethylation is achieved upon reaction of a compound of formula XII-a with BBr$_3$ in an inert solvent such as, but not limited to, dichloromethane or tetrahydrofuran at low temperature to give deprotected compounds of general formula XVII. Alternatively, demethylation can be accomplished upon reaction of compounds of formula XII-a with BF$_3$Me$_2$S complex at ambient temperature in an inert solvent as was mentioned for demethylations using BBr$_3$.

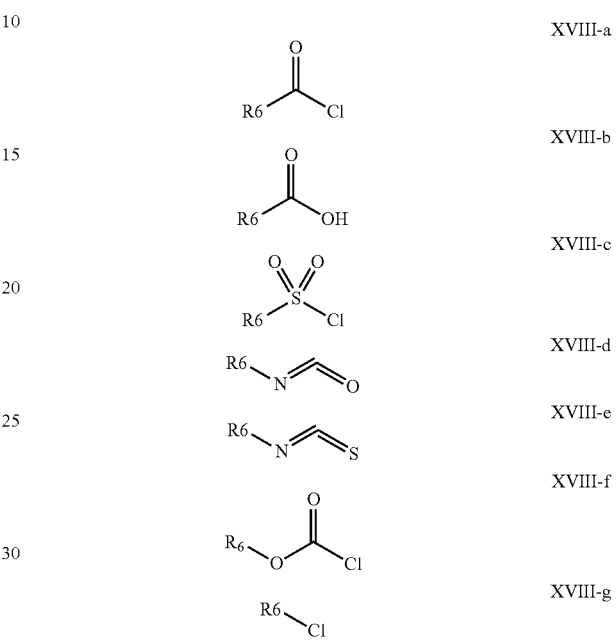

Subsequent functionalizations of the free OH group in derivatives of formula XVII are also well known to those skilled in the art and can be easily established using reagents of formula XVIII-a-g.

For the halide-containing reagents of formula XVIII, the abovementioned reaction is typically conducted at room temperature in a suitable solvent, e.g. an aprotic solvent such as N,N-dimethylformamide, dichloromethane or tetrahydrofuran, in the presence of a base, such as, but not limited to, N,N-diisopropylethylamine or sodium hydride. Additives such as N,N-dimethylaminopyridine or tetrabutylammoniumiodide may accelerate the latter reaction. Furthermore, utilisation of isocyanates or isothiocyanates of formula XVIII-d and XVIII-e in an inert solvent at ambient or elevated temperatures yields compounds of formula I-a wherein Y=NHC(O) or NHC(S), respectively.

Compounds wherein Y=C(O) may also be obtained in an alternative way using carboxylic acids of general formula XVIII-b, using a coupling reagent such as O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU) or bromotripyrrolodinophosphonium hexafluorophosphate (PyBrOP) and a tertiary base, e.g. N,N-diisopropylethylamine, in a solvent such as N,N-dimethylformamide or dichloromethane at ambient or elevated temperature.

Compounds represented by formula I-b-c, in which W=R$^8$,R$^9$N or R$^8$O, respectively, can be synthesized by reacting compounds of general formula XVII with an acid chloride of formula XIX using standard conditions.

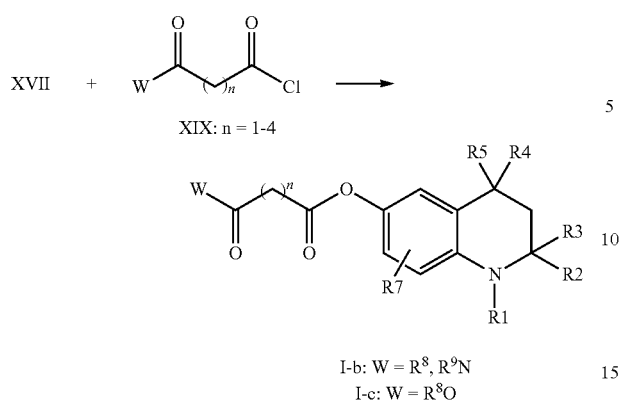

I-b: W = R⁸,R⁹N
I-c: W = R⁸O

Alternatively, compounds of structure I-b-c may be prepared from derivatives of formula XVII and an acid chloride of formula XIX in which W=OEt, followed by base-mediated (e.g NaOH) saponification and subsequent condensation of the free carboxylic acid with either amines of general structure $R^8,R^9NH$ or alcohols of general to structure $R^8OH$ in the presence of a coupling reagent such as the earlier mentioned TBTU, HATU or PyBrOP and a tertiary base such as N,N-diisopropylethylamine.

Compounds represented by formula I-d-e, in which V=$R^8,R^9N$ or $R^8O$, respectively, can be obtained via nucleophilic substitution of a halogen such as Br, present in compounds of formula XXI by amines of general structure $R^8,R^9NH$ or alcohols of general structure $R^8OH$. In turn, the requisite tetrahydroquinoline of formula XXI can be synthesized from a compound of formula XVII and a bromoacylchloride of general structure XX, using art-known synthetic procedures.

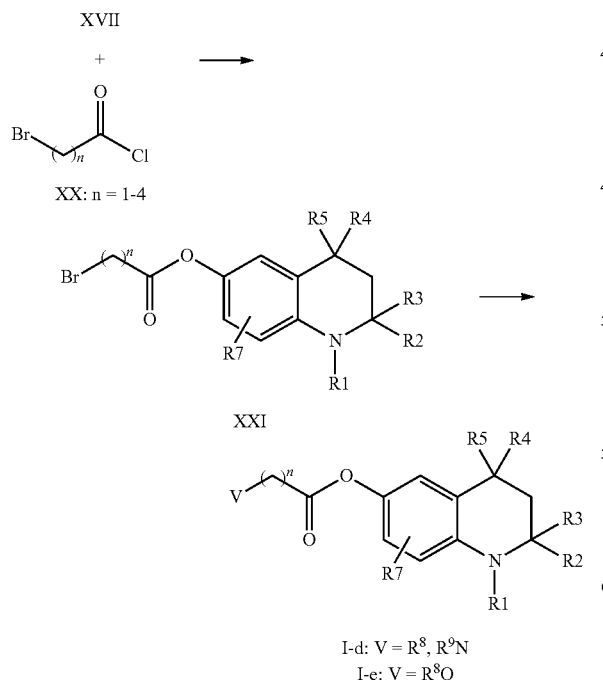

I-d: V = R⁸,R⁹N
I-e: V = R⁸O

Compounds represented by formula I-f-g, in which U=(substituted) heteroaromatic or (substituted) phenyl, respectively, may be prepared via Suzuki coupling of (substituted) iodobenzoylderivatives of formula XXII with boronic acids of general formula XXIII-a-b.

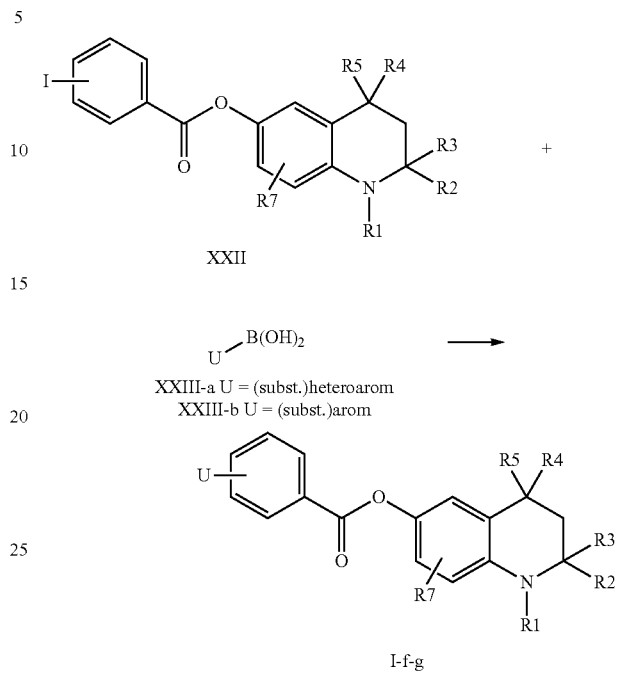

XXIII-a U = (subst.)heteroarom
XXIII-b U = (subst.)arom

I-f-g

In a typical experiment, an iodide of formula XXII is reacted with a boronic acid of formula XXIII-a-b in a solvent mixture such as dim ethoxyethane/ethanol using cesium fluoride and a palladium catalyst such as palladiumtetrakistriphenylphosphine or tris(dibenzylideneacetone)dipalladium at elevated temperature under a nitrogen atmosphere. Addition of triphenylphosphine may accelerate the reaction and improve the yield. The abovementioned reaction is described extensively in literature. See for example: A. Suzuki, Acc. Chem. Res. 15:178, 1982; N. Miyaura, T. Ishiyama, H. Sasaki, M. Ishikawa, M. Satoh and A. Suzuki, J. Am. Chem. Soc. 111:314, 1989.

Likewise, compounds represented by formula I-h wherein X=NH and Y is as previously defined can be synthesized via the same methods as were described above for compounds of general formula Ia-g in which X=O.

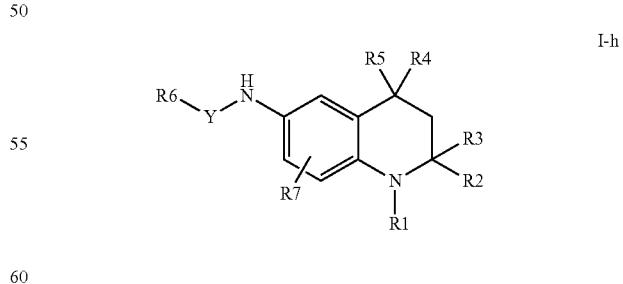

Compounds represented by formula I-i-j in which X=C(O) or S(O)₂ and Y=NH or O, respectively, may be obtained via reaction of the corresponding acyl or sulfonyl chlorides of formula XXV with amines of general structure $R^6NH_2$ or alcohols of general structure $R^6OH$ via the same method as was described earlier for the preparation of compounds of formula I-a.

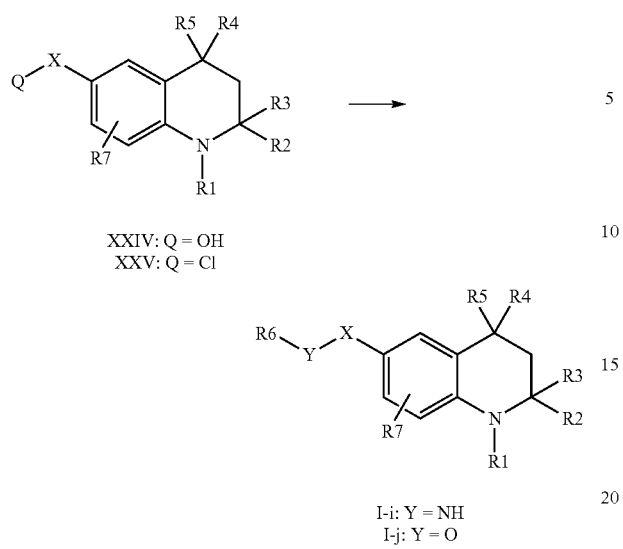

XXIV: Q = OH
XXV: Q = Cl

I-i: Y = NH
I-j: Y = O

The requisite acyl or sulfonyl chlorides of formula XXV can be prepared from the corresponding compounds of formula XXIV by treatment with e.g POCl$_3$, PCl$_5$, oxalylchloride, phosgene or SOCl$_2$, in solvents such as toluene, acetonitrile, or N,N-dimethylformamide, as is described extensively in literature. See for example M. Bonnat, M. Bradley and J. D. Kilburn, Tetrahedron Lett. 37:5409, 1996; J. G. Montana, G. M. Buckley, N. Cooper, H. J. Dyke and L. Gowers, Bioorg. Med. Chem. Lett, 8:2635, 1998; J. Hayler, P. D. Kane, D. LeGrand, F. Lugrin, K. Menear, R. Price, M. Allen, X. Cockcroft, J. Ambler, K. Butler and K. Durren, Bioorg. Med. Chem. Lett. 10:1567, 2000.

Alternatively, compounds of formula XXIV in which X=C(O) can be used directly as starting materials for the preparation of derivatives of formula I-i-j, using coupling reagents as were mentioned previously.

For compounds represented by formula I-k-p, wherein X=C(O) or S(O)$_2$ and Y=NH or O and n=1-4, art-known synthetic procedures can be followed.

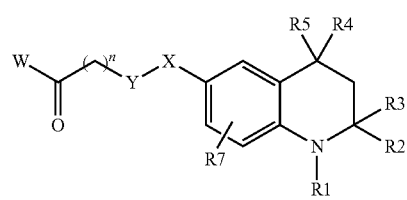

I-k: W = R$^8$, R$^9$N
I-l: W = R$^8$O

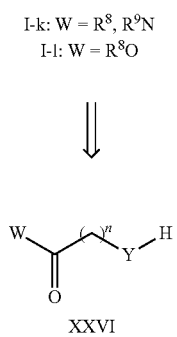

XXVI

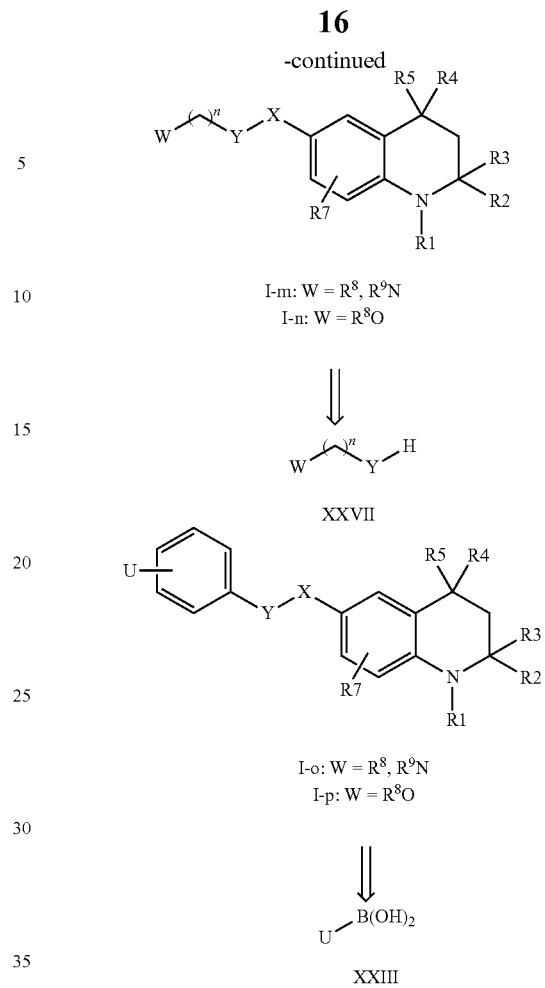

I-m: W = R$^8$, R$^9$N
I-n: W = R$^8$O

XXVII

I-o: W = R$^8$, R$^9$N
I-p: W = R$^8$O

XXIII

Thus, preparation of tetrahydroquinolines of formula I-k-l can be accomplished by condensing an amine or alcohol represented by formula XXVI (Y=NH or O, respectively) with chlorides of general formula XXV using standard conditions. In a similar approach, amines or alcohols of formula XXVII can be utilized to prepare compounds of formula I-m-n. Finally, the use of the earlier mentioned boronic acids XXIII leads to the preparation of compounds of formula I-o-p via the earlier mentioned Suzuki coupling reaction.

Compounds of the present invention wherein X—Y is a bond, represented by formula I-q, can be prepared directly from commercially available or easily preparable anilines of formula XXVIII via the reaction sequence Skraup, acylation and Friedel-Crafts alkylation.

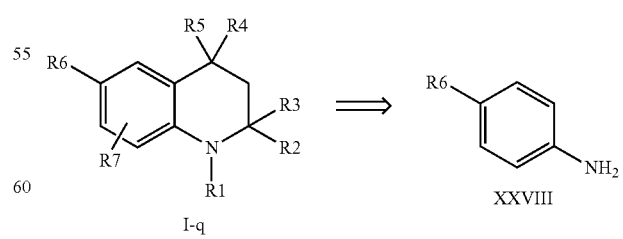

I-q

XXVIII

In another approach, compounds represented by formula I-r in which X—Y is a bond and U=(substituted) heteroaromatic or (substituted) phenyl, may be prepared via Suzuki condensation of the corresponding 6-iodo tetrahydroquinoline derivatives of formula XXIX with boronic acids of general formula XXIII, as was previously mentioned.

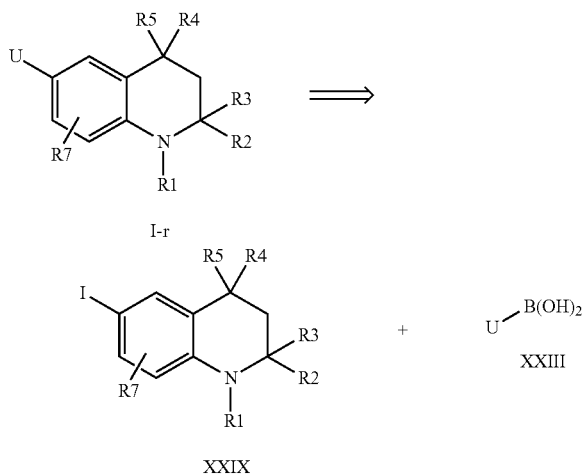

The requisite iodide of formula XXIX can be obtained from the corresponding amine by means of the well-known Sandmeijer reaction.

Some of the compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the present invention possess at least one chiral carbon atom and may therefore be obtained as pure enantiomers, or as a mixture of enantiomers, or as a mixture of diastereomers. Methods for obtaining the pure enantiomers are well known in the art, e.g crystallization of salts which are obtained from optically active acids and the racemic mixture, or chromatography using chiral columns. For diastereomers, straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

For selecting active compounds testing at $10^{-5}$ M must result in an activity of more than 20% of the maximal activity when FSH is used as a reference. Another criterion might be the $EC_{50}$ value which must be $<10^{-5}$ M, preferably $<10^{-7}$ M.

The skilled artisan will recognize that desirable $EC_{50}$ values are dependent on the compound tested. For example, a compound with an $EC_{50}$ which is less than $10^{-5}$ M is generally considered a candidate for drug selection. Preferably this value is lower than $10^{-7}$ M. However, a compound which has a higher $EC_{50}$, but is selective for the particular receptor, may be even a better candidate.

Methods to determine receptor binding, as well as in vitro and in vivo assays to determine biological activity, of gonadotropins are well known. In general, expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759-776, 1991):

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of compound.

For measurement of binding, radioactively labeled or fluorescently labeled compounds may be used. As reference compound human recombinant FSH can be used. In the alternative also competition binding assays can be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be reduced or increased, depending on the inhibitory or stimulating effect of the test compound upon binding to the receptor.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czemilofsky, A. P., (1995) Curr. Opin. Biotechnol. 6:574.

The present invention also relates to a pharmaceutical composition comprising a tetrahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof. The pharmaceutical compositions may also comprise the tetrahydroquinoline derivatives 1-acetyl-6-benzoylamino-4-(4-methylphenyl)-1,2,3,4-tetrahydro-2,2,4-trimethylquinoline, 1-acetyl-4-phenyl-1,2,3,4-tetrahydro-2,2,4,6-tetramethylquinoline, 1-acetyl-4-phenyl-1,2,3,4-tetrahydro-2,2,4,6,8-pentamethylquinoline, 1-acetyl-6-methoxy-4-phenyl-1,2,3,4-tetrahydro-2,2,4-trimethylquinoline, 1-acetyl-6-trifluoroacetylamino-4-(4-methylphenyl)-1,2,3,4-tetrahydro-2,2,4-trimethylquinoline, 1-acetyl-6-trifluoroacetylamino-4-phenyl-1,2,3,4-tetrahydro-2,2,4-trimethylquinoline, 1-acetyl-4-(4-chlorophenyl)-1,2,3,4-tetrahydro-2,2,4,6-tetramethylquinoline and 1-acetyl-4-(4-bromophenyl)-1,2,3,4-tetrahydro-2,2,4,6-tetramethylquinoline.

Compositions include e.g. those suitable for oral, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The tetrahydroquinoline derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO Nobel N.V.).

The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

Thus, the compounds according to the invention can be used in therapy.

A further aspect of the invention resides in the use of a tetrahydroquinoline derivative compound having the general formula I for the manufacture of a medicament to be used for the treatment of disorders responsive to FSH receptor mediated pathways, preferably for the control of fertility, more preferably for the treatment of infertility or to prevent fertility. The compounds according to the invention can also be used for the treatment of hormone-dependent disorders such as breast cancer, prostate cancer and endometriosis.

The invention is illustrated by the following examples.

EXAMPLES

Example 1

1-Acetyl-6-(tert-butoxycarbonyl)amino-4-phenyl-1,2,3,4-tetrahydro-2,2,4-trimethylquinoline (a). 6-(tert-Butoxycarbonyl)amino-1,2-dihydro-2,2,4-trimethylquinoline A mixture of N-Boc-1,4-phenylenediamine (5.0 g) and iodine (1.3 g) in mesityl oxide (25 ml) was stirred at 100° C. for 2 h. The reaction mixture was concentrated in vacuo and the residue was chromatographed on $Al_2O_3$ (Alumina B, act. III) in heptane/dichloromethane=8/2 as eluent.

Yield: 2.9 g. MS-ESI: $[M+H]^+=289.2$ (b). 1-Acetyl-6-(tert-butoxycarbonyl)amino-1,2-dihydro-2,2,4-trimethylquinoline Acetyl chloride (11.1 ml) and acetic anhydride (11.1 ml) were added dropwise to a solution of 6-(tert-butoxycarbonyl)amino-1,2-dihydro-2,2,4-trimethylquinoline (8.5 g) in pyridine (22 ml) and dichloromethane (212 ml). After stirring for 18 h, the reaction mixture was washed with 2 M HCl and water. The organic layer was dried ($MgSO_4$); filtered and concentrated in vacuo. The residue was chromatographed on silicagel in heptane/ethyl acetate=8/2 (v/v) as eluent.

Yield: 6.7 g. MS-ESI: $[M+H]^+=331.2$ (c). 1-Acetyl-6-amino-4-phenyl-1,2,3,4-tetrahydro-2,2,4-trimethylquinoline A mixture of 1-acetyl-6-(tert-butoxycarbonyl)amino-2,2,4-trimethyl-1,2-dihydroquinoline (2.4 g) and $AlCl_3$ (9.5 g) in benzene (150 ml) was stirred at 70° C. for 1 h. The reaction mixture was cooled (0° C.) and quenched with water and in addition a solution of 2 M NaOH was added. The organic layer was separated, dried over $MgSO_4$, filtered and concentrated in vacuo. The residue was chromatographed on silica-gel in heptane/ethyl acetate=8/2 (v/v) as eluent.

Yield: 1.6 g. MS-ESI: [M+H]$^+$=309.2

(d). 1-Acetyl-6-(tert-butoxycarbonyl)amino-4-phenyl-1,2,3,4-tetrahydro-2,2,4-trimethylquinoline A mixture of 1-acetyl-6-amino-4-phenyl-1,2,3,4-tetrahydro-2,2,4-trimethylquinoline (20 mg), (Boc)$_2$O (30 mg) and N,N-diisopropylethylamine (20 l) in tetrahydrofuran (4 ml) was stirred at 60° C. for 18 h. The reaction mixture was concentrated in vacuo and the residue was chromatographed on silicagel in dichloromethane/methanol=1/0=>95/5 (v/v) as eluent.

Yield: 8 mg. MS-ESI: [M+H]$^+$=409.2

Example 2

6-Amino-1-butyryl-4-phenyl-1,2,3,4-tetrahydro-2,2,4-trimethylquinoline (a). 6-(tert-Butoxycarbonyl)amino-1-butyryl-1,2-dihydro-2,2,4-trimethylquinoline Butyryl chloride (185 l) was added dropwise to a solution of 6-(tert-butoxycarbonyl)amino-1,2-dihydro-2,2,4-trimethylquinoline (50 mg) and a catalytic amount of N,N-dimethylaminopyridine in pyridine (4 ml). After stirring for 18 h, the reaction mixture was concentrated in vacuo. The residue was dissolved in ethyl acetate and washed with water. The organic layer was separated, dried (MgSO$_4$) and concentrated in vacuo. The residue was chromatographed on silicagel in heptane/ethyl acetate=1/0=>7/3 (v/v) as eluent.

Yield: 47 mg. MS-ESI: [M+H]$^+$=359.4

(b). 6-Amino-1-butyryl-4-phenyl-1,2,3,4-tetrahydro-2,2,4-trimethylquinoline

A mixture of 1-butyryl-6-(tert-butoxycarbonyl)amino-1,2-dihydro-2,2,4-trimethylquinoline (47 mg) and AlCl$_3$ (52 mg) in benzene (2 ml) was stirred at 60° C. for 6 h. The reaction mixture was cooled (0° C.) and quenched with water and in addition a solution of 2 M NaOH was added. The organic layer was separated, dried over MgSO$_4$ and concentrated in vacuo. The residue was purified by preperative HPLC.

Yield: 10 mg. MS-ESI: [M+H]$^+$=337.2; HPLC: $R_t$=6.97 min. (method 1)

Example 3

1-Acetyl-6-amino-4-(4-chlorophenyl)-1,2,3,4-tetrahydro-2,2,4-trimethylquinoline

A mixture of 1-acetyl-6-(tert-butoxycarbonyl)amino-1,2-dihydro-2,2,4-trimethylquinoline (25 mg) and AlCl$_3$ (35 mg) in chlorobenzene (2 ml) was stirred for 1 h. The reaction mixture was quenched with water and in addition a solution of 2 M NaOH and ethyl acetate were added. The organic layer was separated, dried over MgSO$_4$ and concentrated in vacuo.

Yield: 20 mg. MS-ESI: [M+H]$^+$=343.4; HPLC: $R_t$=6.16 min. (method 1)

Example 4

1-Acetyl-6-amino-4-(4-fluorophenyl)-1,2,3,4-tetrahydro-2,2,4-trimethylquinoline

Friedel-Crafts alkylation of fluorobenzene (2 ml) with 1-acetyl-6-(tert-butoxycarbonyl)amino-1,2-dihydro-2,2,4-trimethylquinoline (25 mg) in the presence of AlCl$_3$ (35 mg) was performed according to the method described in example 3.

Yield: 15 mg. MS-ESI: [M+H]$^+$=327.4; HPLC: $R_t$=5.63 min. (method 1)

Example 5

1-Acetyl-6-amino-1,2,3,4-tetrahydro-4-(4-toloyl)-2,2,4-trimethylquinoline

Friedel-Crafts alkylation of toluene (2 ml) with 1-acetyl-6-(tert-butoxycarbonyl)amino-1,2-dihydro-2,2,4-trimethylquinoline (25 mg) in the presence of AlCl$_3$ (35 mg) was performed according to the method described in example 3.

Yield: 22 mg. MS-ESI: [M+H]$^+$=323.2

Example 6

1-Acetyl-6-(4-chlorobenzoyl)amino-4-phenyl-1,2,3,4-tetrahydro-2,2,4-trimethylquinoline A mixture of 1-acetyl-6-amino-4-phenyl-1,2,3,4-tetrahydro-2,2,4-trimethylquinoline (10 mg), 4-chlorobenzoyl chloride (11 mg) and N,N-diisopropylethylamine (22 l) in tetrahydrofuran (1 ml) was stirred for 18 h. The reaction mixture was concentrated in vacuo, the residue was dissolved in ethyl acetate and washed with 0.5 HCl, water, 5% aq. NaHCO$_3$, water and brine. The organic layer was separated, dried (MgSO$_4$) and concentrated in vacuo. The residue was chromatographed on silicagel in heptane/ethyl acetate=1/0=>0/1 (v/v) as eluent.

Yield: 9.5 mg. MS-ESI: [M+H]$^+$=447.4; HPLC: $R_t$=10.87 min. (method 1)

Example 7

1-Acetyl-6-benzoylamino-4-phenyl-1,2,3,4-tetrahydro-2,2,4-trimethylquinoline

Acylation of 1-acetyl-6-amino-4-phenyl-1,2,3,4-tetrahydro-2,2,4-trimethylquinoline (10 mg) with benzoyl chloride (9.1 mg) and N,N-diisopropylethylamine (22 l) in tetrahydrofuran (1 ml) was performed according to the method described in example 6.

Yield: 1.2 mg. MS-ESI: [M+H]$^+$=413.4; HPLC: $R_t$=10.01 min. (method 1)

Example 8

1-Acetyl-4-phenyl-1,2,3,4-tetrahydro-6-(4-[trifluoromethyl]benzoyl)amino-2,2,4-trimethylquinoline Acylation of 1-acetyl-6-amino-4-phenyl-1,2,3,4-tetrahydro-2,2,4-trimethylquinoline (10 mg) with 4-trifluoromethylbenzoyl chloride (14 mg) and N,N-diisopropylethylamine (22 l) in tetrahydrofuran (1 ml) was performed according to the method described in example 6.

Yield: 8.9 mg. MS-ESI: [M+H]$^+$=481.4; HPLC: $R_t$=10.76 min. (method 1)

Example 9

1-Acetyl-6-(4-nitrobenzoyl)amino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (10 mg) with 4-nitrobenzoyl chloride (12 mg) and N,N-diisopropylethylamine (22 l) in tetrahydrofuran (1 ml) was performed according to the method described in example 6.

Yield: 8.2 mg. MS-ESI: [M+H]$^+$=458.4; HPLC: R$_t$=10.02 min. (method 1)

Example 10

1-Acetyl-4-phenyl-6-(4-n-propylbenzoyl)amino-1,2,3,4-tetrahydro-2,2,4-trimethylquinoline Acylation of 1-acetyl-6-amino-4-phenyl-1,2,3,4-tetrahydro-2,2,4-trimethylquinoline (10 mg) with 4-n-propylbenzoyl chloride (12 mg) and N,N-diisopropylethylamine (22 l) in tetrahydrofuran (1 ml) was performed according to the method described in example 6.

Yield: 6.7 mg. MS-ESI: [M+H]$^+$=455.4; HPLC: R$_t$=11.19 min. (method 1)

Example 11

1-Acetyl-6-(3-bromo-2,6-dimethoxybenzoyl)amino-4-phenyl-1,2,3,4-tetrahydro-2,2,4-trimethylquinoline A mixture of 1-acetyl-6-amino-4-phenyl-1,2,3,4-tetrahydro-2,2,4-trimethylquinoline (25 mg), 3-bromo-2,6-dimethoxybenzoic acid (23 mg), O-(7-azabenzotriazol-1-yl)-N,N,N',N'-tetramethyluronium hexafluorophosphate (HATU) (68 mg) and N,N-diisopropylethylamine (32 l) in dichloromethane (4 ml) was stirred for 18 h. The reaction mixture was concentrated in vacuo, the residue was dissolved in ethyl acetate and washed with 0.5 M HCl, water, 5% aq. NaHCO$_3$, water and brine. The organic layer was dried (MgSO$_4$) and concentrated in vacuo. The residue was chromatographed on silicagel in heptane/ethyl acetate=1/0=>0/1 (v/v) as eluent.

Yield: 28 mg. MS-ESI: [M+H]$^+$=551.4; HPLC: R$_t$=3.75 min. (method 2)

Example 12

1-Acetyl-4-phenyl-6-(4-phenylbenzoyl)amino-1,2,3,4-tetrahydro-2,2,4-trimethylquinoline Acylation of 1-acetyl-6-amino-4-phenyl-1,2,3,4-tetrahydro-2,2,4-trimethylquinoline (11 mg) with 4-biphenylcarbonyl chloride (16 mg) and N,N-diisopropylethylamine (22 μl) in tetrahydrofuran (1 ml) was performed according to the method described in example 6.

Yield: 1.0 mg. MS-ESI: [M+H]$^+$=489.4; HPLC: R$_t$=11.62 min. (method 1)

Example 13

1-Acetyl-6-(4-[4-chlorophenyl]benzoyl)amino-4-phenyl-1,2,3,4-tetrahydro-2,2,4-trimethylquinoline (a). 1-Acetyl-6-(4-iodobenzoyl)amino-4-phenyl-1,2,3,4-tetrahydro-2,2,4-trimethylquinoline A mixture of 1-acetyl-6-amino-4-phenyl-1,2,3,4-tetrahydro-2,2,4-trimethylquinoline (300 mg), 4-iodobenzoyl chloride (520 mg) and a catalytic amount of N,N-dimethylaminopyridine in pyridine (4 ml) was stirred for 18 h. The reaction mixture was concentrated in vacuo, the residue was dissolved in ethyl acetate and washed with saturated aq. NaHCO$_3$, water and brine. The organic layer was dried (MgSO$_4$) and concentrated in vacuo.

Yield: 460 mg. MS-ESI: [M+H]$^+$=539.4; HPLC: R$_t$=10.98 min. (method 1)

(b). 1-Acetyl-6-(4-[4-chlorophenyl]benzoyl)amino-4-phenyl-1,2,3,4-tetrahydro-2,2,4-trimethylquinoline A mixture of 1-acetyl-6-(4-iodobenzoyl)amino-4-phenyl-1,2,3,4-tetrahydro-2,2,4-trimethylquinoline (25 mg), 4-chlorobenzeneboronic acid (22 mg), cesium fluoride (14 mg), triphenylphosphine (5.0 mg) and tris(dibenzylideneacetone)dipalladium(0). (4.3 mg) in dimethoxyethane/ethanol 4:1 (5 ml) was stirred for 15 min. as nitrogen was bubbled through the solution. After 3 h. at 80° C. the reaction mixture was concentrated in vacuo, the residue was dissolved in ethyl acetate and washed with 0.5 M HCl, water, 5% aq. NaHCO$_3$, water and brine. The organic layer was dried (MgSO$_4$) and concentrated in vacuo. The residue was chromatographed on silicagel in heptane/ethyl acetate=1/0=>0/1 (v/v) as eluent.

Yield: 16 mg. MS-ESI: [M+H]$^+$=523.4; HPLC: R$_t$=4.40 min. (method 2)

Example 14

1-Acetyl-4-phenyl-6-(4-[3-pyridyl]benzoyl)amino-1,2,3,4-tetrahydro-2,2,4-trimethylquinoline Suzuki cross-coupling of 1-acetyl-6-(4-iodobenzoyl)amino-4-phenyl-1,2,3,4-tetrahydro-2,2,4-trimethylquinoline (25 mg), pyridine-3-boronic acid-1,3-propanediol cyclic ester (23 mg), cesium fluoride (14 mg), triphenylphosphine (5.0 mg) and tris(dibenzylideneacetone)dipalladium(0) (4.3 mg) in dimethoxyethane/ethanol 4:1 (v/v) (5 ml) was performed according to the method described in example 13.

Yield: 17 mg. MS-ESI: [M+H]$^+$=490.4; HPLC: R$_t$=7.11 ruin. (method 1)

Example 15

1-Acetyl-4-phenyl-6-(2-phenyl-5-methoxybenzoyl)amino-1,2,3,4-tetrahydro-2,2,4-trimethylquinoline (a). 1-Acetyl-6-(2-bromo-5-methoxybenzoyl)amino-4-phenyl-1,2,3,4-tetrahydro-2,2,4-trimethylquinoline Condensation of 1-acetyl-6-amino-4-phenyl-1,2,3,4-tetrahydro-2,2,4-trimethylquinoline (25 mg) with 2-bromo-5-methoxybenzoic acid (21 mg) under the agency of HATU (68 mg) and N,N-diisopropylethylamine (32 l) in dichloromethane (4 ml) was performed according to the method described in example 11., Yield: 31 mg. MS-ESI: [M+H]$^+$=521.4; HPLC: R$_t$=3.74 min. (method 2)

(b). 1-Acetyl-4-phenyl-6-(2-phenyl-5-methoxybenzoyl)amino-1,2,3,4-tetrahydro-2,2,4-trimethylquinoline Suzuki cross-coupling of 1-acetyl-4-phenyl-6-(2-bromo-5-methoxybenzoyl)amino-1,2,3,4-tetrahydro-2,2,4-trimethylquinoline (30 mg), benzeneboronic acid (25 mg), cesium fluoride (21 mg), triphenylphosphine (7.0 mg) and tris(dibenzylideneacetone)dipalladium(0) (6.0 mg) in dimethoxyethane/ethanol 4:1 (v/v) (5 ml) was performed according to the method described in example 13.

Yield: 23 mg. MS-ESI: [M+H]$^+$=519.4; HPLC: R$_t$=10.87 min. (method 1)

Example 16

1-Acetyl-4-phenyl-6-(2-phenyl-3-methylbenzoyl) amino-1,2,3,4-tetrahydro-2,2,4-trimethylquinoline (a). 1-Acetyl-4-phenyl-6-(2-bromo-3-methylbenzoyl)amino-1,2,3,4-tetrahydro-2,2,4-trimethylquinoline Condensation of 1-acetyl-6-amino-4-phenyl-1,2,3,4-tetrahydro-2,2,4-trimethylquinoline (25 mg) with 2-bromo-3-methylbenzoic acid (19 mg) under the agency of HATU (68 mg) and N,N-diisopropylethylamine (32 l) in dichloromethane (4 ml) was performed according to the method described in example 11.
Yield: 16.3 mg. MS ESI: [M+H]$^+$=505.2; HPLC: R$_t$=3.80 min. (method 2)

(b). 1-Acetyl-4-phenyl-6-(2-phenyl-3-methylbenzoyl)amino-1,2,3,4-tetrahydro-2,2,4-trimethylquinoline Suzuki cross-coupling of 1-acetyl-4-phenyl-6-(2-bromo-3-methylbenzoyl)amino-1,2,3,4-tetrahydro-2,2,4-trimethylquinoline (16 mg), benzeneboronic acid (25 mg), cesium fluoride (21 mg), triphenylphosphine (7.0 mg) and tris(dibenzylideneacetone)dipalladium(0) (6.0 mg) in dimethoxyethane/ethanol 4:1 (v/v) (5 ml) was performed according to the method described in example 13.
Yield: 4.9 mg. MS-ESI: [M+H]$^+$=503.3; HPLC: R$_t$=4.61 min (method 2)

Example 17

1-Acetyl-4-phenyl-1,2,3,4-tetrahydro-6-(-toluenesulfonyl)amino-2,2,4-trimethylquinoline Sulfonylation of 1-acetyl-6-amino-4-phenyl-1,2,3,4-tetrahydro-2,2,4-trimethylquinoline (10 mg) with -toluenesulfonyl chloride (12 mg) and N,N-diisopropylethylamine (22 l) in tetrahydrofuran (25 ml) was performed according to the acylation method described in example 6.
Yield: 9.8 mg. MS-ESI: [M+H]$^+$=463.4; HPLC: R$_t$=9.49 min. (method 1)

Example 18

1-Acetyl-4-phenyl-6-(phenylaminocarbonyl)amino-1,2,3,4-tetrahydro-2,2,4-trimethylquinoline A mixture of 1-acetyl-6-amino-4-phenyl-1,2,3,4-tetrahydro-2,2,4-trimethylquinoline (10 mg), phenyl isocyanate (8.0 mg) and N,N-diisopropylethylamine (22 l) in tetrahydrofuran (1 ml) was stirred for 18 h. The reaction mixture was concentrated in vacuo, the residue was dissolved in ethyl acetate and washed with 0.5 M HCl, water, 5% aq. NaHCO$_3$, water and brine. The organic layer was dried (MgSO$_4$) and concentrated in vacuo. The residue was chromatographed on silicagel in heptane/ethyl acetate=1/0=>0/1 (v/v) as eluent.
Yield: 3.8 mg. MS-ESI: [M+H]$^+$=428.4; HPLC: R$_t$=10.39 min. (method 1)

Example 19

1-Acetyl-6-(tert-butylaminothiocarbonyl)amino-4-phenyl-1,2,3,4-tetrahydro-2,2,4-trimethylquinoline Thiourea formation of 1-acetyl-6-amino-4-phenyl-1,2,3,4-tetrahydro-2,2,4-trimethylquinoline (10 mg) with tert-butyl isothiocyanate (7.5 mg) and N,N-diisopropylethylamine (22 l) in tetrahydrofuran (1 ml) was performed according to the method described in example 18.
Yield: 0.50 mg. MS-ESI: [M+H]$^+$=424.4; HPLC: R$_t$=5.90 min. (method 1)

Example 20

1-Acetyl-6-(4-tert-butylbenzyl)amino-4-phenyl-1,2,3,4-tetrahydro-2,2,4-trimethylquinoline trifluoroacetic acid A mixture of 1-acetyl-6-amino-4-phenyl-1,2,3,4-tetrahydro-2,2,4-trimethylquinoline (10 mg), 4-(tert-butyl)benzylchloride (6.5 mg) and N,N-diisopropylethylamine (10 l) in tetrahydrofuran (1 ml) was stirred at 50° C. for 18 h. The reaction mixture was concentrated in vacuo, the residue was dissolved in ethyl acetate and washed with 0.5 HCl, water, 5% aq. NaHCO$_3$, water and brine. The organic layer was dried (MgSO$_4$) and concentrated in vacuo. The residue was chromatographed on silicagel in heptane/ethyl acetate=1/0=>0/1 (v/v) as eluent.
Yield: 3.1 mg. MS-ESI: [M+H]$^+$=455.4; HPLC: R$_t$=10.00 min. (method 1)

Example 21

1-Acetyl-4-phenyl-6-(3-phenylpropionyl)amino-1,2,3,4-tetrahydro-2,2,4-trimethylquinoline Acylation of 1-acetyl-6-amino-4-phenyl-1,2,3,4-tetrahydro-2,2,4-trimethylquinoline (10 mg) with 3-phenylpropionyl chloride (11 mg) and N,N-diisopropylethylamine (22 l) in tetrahydrofuran (1 ml) was performed according to the method described in example 6.
Yield: 1.2 mg. MS-ESI: [M+H]$^+$=441.4; HPLC: R$_t$=10.25 min. (method 1)

Example 22

1-Acetyl-6-(2-furoyl)amino-4-phenyl-1,2,3,4-tetrahydro-2,2,4-trimethylquinoline

Acylation of 1-acetyl-6-amino-4-phenyl-1,2,3,4-tetrahydro-2,2,4-trimethylquinoline (10 mg) with 2-furoyl chloride (8.5 mg) and N,N-diisopropylethylamine (22 l) in tetrahydrofuran (1 ml) was performed according to the method described in example 6.
Yield: 7.7 mg. MS-ESI: [M+H]$^+$=403.4; HPLC: R$_t$=8.91 min. (method 1)

Example 23

1-Acetyl-6-(isovaleryl)amino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (10 mg) with isovaleryl chloride (7.8 mg) and N,N-diisopropylethylamine (22 l) in tetrahydrofuran (1 ml) was performed according to the method described in example 6.

Yield: 5.3 mg. MS-ESI: [M+H]$^+$=393.4; HPLC: R$_t$=9.35 min. (method 1).

Example 24

1-Acetyl-6-(3-[adamantan-1-yl]propionyl)amino-4-phenyl-1,2,3,4-tetrahydro-2,2,4-trimethylquinoline Condensation of 1-acetyl-6-amino-4-phenyl-1,2,3,4-tetrahydro-2,2,4-trimethylquinoline (10 mg) with 3-(adamantan-1-yl)propionic acid (10 mg) under the agency of HATU (25 mg) and N,N-diisopropylethylamine (22 l) in dichloromethane (1 ml) was performed according to the method described in example 11.

Yield: 6.7 mg. MS-ESI: [M+H]$^+$=499.4; HPLC: R$_t$=12.43 min. (method 1)

Example 25

1-Acetyl-6-(ethyl malonyl)amino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (150 mg) with ethyl malonyl chloride (147 mg) and N,N-diisopropylethylamine (314 l) in tetrahydrofuran (8 ml) was performed according to the method described in example 6.

Yield: 163 mg. MS-ESI: [M+H]$^+$=423.2; HPLC: R$_t$=8.48 min. (method 1)

Example 26

1-Acetyl-6-([4-methoxybenzylamino]carbonylmethylcarbonyl)amino-4-phenyl-1,2,3,4-tetrahydro-2,2,4-trimethylquinoline (a). 1-Acetyl-6-(hydroxycarbonylmethylcarbonyl)amino-4-phenyl-1,2,3,4-tetrahydro-2,2,4-trimethylquinoline A 2 M NaOH solution was added dropwise to a stirred solution of 1-acetyl-6-(ethyl malonyl)amino-4-phenyl-1,2,3,4-tetrahydro-2,2,4-trimethylquinoline (161 mg) in dioxane/water 4:1 (v/v) (12 ml) until pH 14. After stirring for 3.5 h, the reaction mixture was poured into water and extracted with ethyl acetate at pH 2. The organic layer was washed with water and brine, dried (MgSO$_4$) and concentrated in vacuo.

Yield: 163 mg. MS-ESI: [M+H]$^+$=395.2; HPLC: R$_t$=7.43 min. (method 1)

(b). 1-Acetyl-6-([4-methoxybenzylamino]carbonylmethylcarbonyl)amino-4-phenyl-1,2,3,4-tetrahydro-2,2,4-trimethylquinoline Condensation of 4-methoxybenzylamine (5.2 mg) with 1-acetyl-6-(hydroxycarbonylmethylcarbonyl)amino-4-phenyl-1,2,3,4-tetrahydro-2,2,4-trimethylquinoline (10 mg), under the agency of HATU (19 mg) and N,N-diisopropylethylamine (16 l) in tetrahydrofuran (2 ml) was performed according to the method described in example 11.

Yield: 7.3 mg. MS-ESI: [M+H]$^+$=514.4; HPLC: R$_t$=8.80 min. (method 1)

Example 27

1-Acetyl-6-([ethoxycarbonylmethylamino]carbonylmethylcarbonyl)amino-4-phenyl-1,2,3,4-tetrahydro-2,2,4-trimethylquinoline Condensation of glycine ethyl ester.HCl (5.3 mg) with 1-acetyl-6-(hydroxycarbonylmethylcarbonyl)amino-4-phenyl-1,2,3,4-tetrahydro-2,2,4-trimethylquinoline (10 mg), under the agency of HATU (19 mg) and N,N-diisopropylethylamine (16 l) in tetrahydrofuran (2 ml) was performed according to the method described in example 11.

Yield: 4.6 mg. MS-ESI: [M+H]$^+$=480.6; HPLC: R$_t$=7.94 min. (method 1)

Example 28

1-Acetyl-6-([N-ethyl-N-benzylamino]carbonylmethylcarbonyl)amino-4-phenyl-1,2,3,4-tetrahydro-2,2,4-trimethylquinoline Condensation of N-ethylbenzylamine (5.2 mg) with 1-acetyl-6-(hydroxycarbonylmethylcarbonyl)amino-4-phenyl-1,2,3,4-tetrahydro-2,2,4-trimethylquinoline (10 mg), under the agency of HATU (19 mg) and N,N-diisopropylethylamine (16 l) in tetrahydrofuran (2 ml) was performed according to the method described in example 11.

Yield: 7.3 mg. MS-ESI: [M+H]$^+$=512.6; HPLC: R$_t$=9.36 min. (method 1)

Example 29

1-Acetyl-6-([2,4-difluorobenzylamino]methylcarbonyl)amino-4-phenyl-1,2,3,4-tetrahydro-2,2,4-trimethylquinoline (a). 1-Acetyl-6-(bromoacetyl)amino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (130 mg) with bromoacetyl chloride (69 l) and N,N-diisopropylethylamine (121 l) in dichloromethane (10 ml) was performed according to the method described in example 6.

Yield: 151 mg. MS-ESI: [M+H]$^+$=431.2

(b). 1-Acetyl-6-([2,4-difluorobenzylamino]methylcarbonyl)amino-4-phenyl-1,2,3,4-tetrahydro-2,2,4-trimethylquinoline A mixture of 1-acetyl-6-(bromoacetyl)amino-4-phenyl-1,2,3,4-tetrahydro-2,2,4-trimethylquinoline (10 mg), 2,4-difluorobenzylamine (6.0 mg) and N,N-diisopropylethylamine (10 l) in dioxane (2 ml) was stirred at 40° C. for 18 h. The reaction mixture was concentrated in vacuo. The residue was chromatographed on silicagel in dichloromethane/methanol=1/0=>95/5 (v/v) as eluent.

Yield: 5.5 mg. MS-ESI: [M+H]$^+$=492.4; HPLC: R$_t$=6.74 min. (method 1)

Example 30

1-Acetyl-6-([4-{1-phenyl}-piperazinyl]methylcarbonyl)amino-4-phenyl-1,2,3,4-tetrahydro-2,2,4-trimethylquinoline N-Alkylation of 1-phenylpiperazine (7.0 l) with 1-acetyl-6-(bromoacetyl)amino-4-phenyl-1,2,3,4-tetrahydro-2,2,4- trimethylquinoline (10 mg) and N,N-diisopropylethylamine (10 l) in dioxane (2 ml) was performed according to the method described in example 29.
Yield: 8.4 mg. MS-ESI: [M+H]$^+$=511.4; HPLC: R$_t$=7.01 min. (method 1)

Example 31

1-Acetyl-6-([N-morpholino]methylcarbonyl)amino-4-phenyl-1,2,3,4-tetrahydro-2,2,4-trimethylquinoline N-Alkylation of morpholine (4.0 l) with 1 acetyl-6-(bromoacetyl)amino-4-phenyl-1,2,3,4-tetrahydro-2,2,4-trimethylquinoline (10 mg) and N,N-diisopropylethylamine (9.0 l) in dichloromethane (2 ml) was performed according to the method described in example 29.
Yield: 10 mg. MS-ESI: [M+H]$^+$=436.4; HPLC: R$_t$=5.64 min. (method 1)

Example 32

1-Acetyl-6-(2-thiophenemethylamino)carbonyl-4-phenyl-1,2,3,4-tetrahydro-2,2,4-trimethylquinoline (a). 1,2-dihydro-2,2,4-trimethylquinoline-6-carboxylic acid methyl ester Skraup reaction of methyl 4-aminobenzoate (5.0 g) and iodine (1.7 g) in mesityl oxide (25 ml) was performed according to the method described in example 1.
Yield: 2.3 g. MS-ESI: [M+H]$^+$=232.2

(b). 1-Acetyl-1,2-dihydro-2,2,4-trimethylquinoline-6-carboxylic acid methyl ester A mixture of 1,2-dihydro-2,2,4-trimethylquinoline-6-carboxylic acid methyl ester (2.3 g) and a catalytic amount of N,N-dimethylaminopyridine in acetic anhydride (60 ml) was stirred at 100° C. for 18 h. The reaction mixture was concentrated in vacuo, the residue was dissolved in ethyl acetate and washed with water and brine. The organic layer was dried (MgSO$_4$) and concentrated in vacuo. The residue was chromatographed on silicagel in heptane/ethyl acetate=1/1=>1/9 (v/v) as eluent.
Yield: 2.3 g.

(c). 1-Acetyl-4-phenyl-1,2,3,4-tetrahydro-2,2,4-trimethylquinoline-6-carboxylic acid methyl ester Friedel-Crafts alkylation of benzene (60 ml) with 1-acetyl-1,2-dihydro-2,2,4-s trimethylquinoline-6-carboxylic acid methyl ester (2.3 g) in the presence of AlCl$_3$ (4.4 g) was performed according to the method described in example 3.
Yield: 1.2 g. MS-ESI: [M+H]$^+$=352.4; HPLC: R$_t$=9.72 min. (method 1)

(d). 1-Acetyl-4-phenyl-1,2,3,4-tetrahydro-2,2,4-trimethylquinoline-6-carboxylic acid A 2 M NaOH solution was added dropwise to a stirred solution of 1-acetyl-4-phenyl-1,2,3,4-tetrahydro-2,2,4-trimethylquinoline-6-carboxylic acid methyl ester (1.2 g) in dioxane/water 4:1 (v/v) (50 ml) until pH 12. After stirring for 18 h, the reaction mixture was poured into water and extracted with ethyl acetate at pH 2. The organic layer was washed with water and brine, dried (MgSO$_4$) and concentrated in vacuo.
Yield: 891 mg. MS-ESI: [M+H]$^+$=338.2

(e). 1-Acetyl-6-(2-thiophenemethylamino)carbonyl-4-phenyl-1,2,3,4-tetrahydro-2,2,4-trimethylquinoline Condensation of 2-thiophenemethylamine (5.0 mg) with 1-acetyl-4-phenyl-1,2,3,4-tetrahydro-2,2,4-trimethylquinoline-6-carboxylic acid (10 mg), user the agency of HATU (23 mg) and N,N-diisopropylethylamine (19 l) in dichloromethane (2 ml) was performed according to the method described in example 11.
Yield: 3.0 mg. MS-ESI: [M+H]$^+$=433.4; HPLC: R$_t$=9.28 min. (method 1)

Example 33

1-Acetyl-6-(2-[4-methoxyphenyl]ethylamino)carbonyl-4-phenyl-1,2,3,4-tetrahydro-2,2,4-trimethylquinoline Condensation of 2-(4-methoxyphenyl)ethylamine (6.1 mg) with 1-acetyl-4-phenyl-1,2,3,4-tetrahydro-2,2,4-trimethylquinoline-6-carboxylic acid (10 mg), under the agency of HATU (23 mg) and N,N-diisopropylethylamine (19 l)) in dichloromethane (2 ml) was performed according to the method described in example 11.
Yield: 9.9 mg. MS-ESI: [M+H]$^+$=457.4; HPLC: R$_t$=9.34 min. (method 1)

Example 34

1-Acetyl-6-(3-isopropoxypropylamino)carbonyl-4-phenyl-1,2,3,4-tetrahydro-2,2,4-trimethylquinoline Condensation of 3-isopropoxypropylamine (5.2 mg) with 1-acetyl-4-phenyl-1,2,3,4-tetrahydro-2,2,4-trimethylquinoline-6-carboxylic acid (10 mg), under the agency of HATU (23 mg) and N,N-diisopropylethylamine (19 l) in dichloromethane (2 ml) was performed according to the method described in example 11.
Yield: 8.8 mg. MS-ESI: [M+H]$^+$=437.4; HPLC: R$_t$=8.80 min. (method 1)

Example 35

1-Acetyl-6-(2-[methylthio]ethylamino)carbonyl-4-phenyl-1,2,3,4-tetrahydro-2,2,4-trimethylquinoline Condensation of 2-(methylthio)ethylamine (4.1 mg) with 1-acetyl-4-phenyl-1,2,3,4-tetrahydro-2,2,4-trimethylquinoline-6-carboxylic acid (10 mg), under the agency of HATU (23 mg) and N,N-diisopropylethylamine (19 l) in dichloromethane (2 ml) was performed according to the method described in example 11.
Yield: 10 mg. MS-ESI: [M+H]$^+$=411.4; HPLC: R$_t$=3.33 min. (method 2)

Example 36

1-Acetyl-6-(4-methoxybenzyloxy)carbonyl-4-phenyl-1,2,3,4-tetrahydro-2,2,4-trimethylquinoline Condensation of 4-methoxybenzyl alcohol (6.2 mg) with 1-acetyl-4-phenyl-1,2,3,4-tetrahydro-2,2,4-trimethylquinoline-6-carboxylic acid (10 mg), under the agency of HATU (23 mg) and N,N-diisopropylethylamine (19 l) in dichloromethane (2 ml) was performed according to the method described in example 11.

Yield: 7.2 mg. MS-ESI: [M+H]$^+$=458.4; HPLC: R$_t$=3.90 min. (method 2)

Example 37

1-Acetyl-6-(4-phenylbenzoyl)oxy-4-phenyl-1,2,3,4-tetrahydro-2,2,4-trimethylquinoline (a). 1,2-Dihydro-6-methoxy-2,2,4-trimethylquinoline Skraup reaction of 4-anisidine (5.0 g) and iodine (1.7 g) in mesityl oxide (25 ml) was performed according to the method described in example 1.

Yield: 2.3 g. MS-ESI: [M+H]$^+$=204.2

(b). 1-Acetyl-1,2-dihydro-6-methoxy-2,2,4-trimethylquinoline

Acetyl chloride (8 ml) was added dropwise to a cooled (0° C.) solution of 1,2-dihydro-6-methoxy-2,2,4-trimethylquinoline (1.7 g) and a catalytic amount of N,N-dimethylaminopyridine in pyridine (60 ml). After stirring for 18 h, the reaction mixture was concentrated in vacuo. The residue was dissolved in dichloromethane and washed with 1 M HCl, water, 5% aq. NaHCO$_3$, water and brine. The organic layer was dried (MgSO$_4$) and concentrated in vacuo. The residue was chromatographed on silicagel in dichloromethane as eluent.

Yield: 1.8 g. MS-ESI: [M+H]$^+$=246.2

(c). 1-Acetyl-6-methoxy-4-phenyl-1,2,3,4-tetrahydro-2,2,4-trimethylquinoline

Fiedel-Crafts alkylation of benzene (25 ml) with 1-acetyl-1,2-dihydro-6-methoxy-2,2,4-trimethylquinoline (1.8 g) in the presence of AlCl$_3$ (3.0 g) was performed according to the method described in example 3.

Yield: 1.9 g. R$_t$=9.62 min. (method 1)

(d). 1-Acetyl-6-hydroxy-4-phenyl-1,2,3,4-tetrahydro-2,2,4-trimethylquinoline

Boron tribromide (1.30 ml) was added dropwise to a cooled (0° C.) solution of 1-acetyl-6-methoxy-4-phenyl-1,2,3,4-tetrahydro-2,2,4-trimethylquinoline (0.9 g) in dichloromethane (75 ml). After stirring for 18 h, the reaction mixture was poured into water and extracted with ethyl acetate. The organic layer was washed with water, 5% aq. NaHCO$_3$ and water, dried (MgSO$_4$) and concentrated in vacuo.

Yield: 950 mg. MS-ESI: [M+H]$^+$=310.2; HPLC: R$_t$=8.41 min. (method 1)

(e). 1-Acetyl-4-phenyl-6-(4-phenylbenzoyl)oxy-1,2,3,4-tetrahydro-2,2,4-trimethylquinoline Acylation of 1-acetyl-6-hydroxy-4-phenyl-1,2,3,4-tetrahydro-2,2,4-trimethylquinoline (10 mg) with 4-biphenylcarbonyl chloride (14 mg) and N,N-diisopropylethylamine (28 l) in tetrahydrofuran (1 ml) was performed according to the method described in example 6.

Yield: 8.2 mg. MS-ESI: [M+H]$^+$=490.4; HPLC: R$_t$=12.81 min. (method 1)

Example 38

1-Acetyl-6-(tert-butylacetyl)oxy-4-phenyl-1,2,3,4-tetrahydro-2,2,4-trimethylquinoline Acylation of 1-acetyl-6-hydroxy-4-phenyl-1,2,3,4-tetrahydro-2,2,4-trimethylquinoline (10 mg) with tert-butylacetyl chloride (9.0 l) and N,N-diisopropylethylamine (28 l) in tetrahydrofuran (1 ml) was performed according to the method described in example 6.

Yield: 3.9 mg. MS-ESI: [M+H]$^+$=408.4; HPLC: R$_t$=11.28 min. (method 1)

Example 39

1-Acetyl-6-(cyclopropylmethyl)oxy-4-phenyl-1,2,3,4-tetrahydro-2,2,4-trimethylquinoline A mixture of 1-acetyl-6-hydroxy-4-phenyl-1,2,3,4-tetrahydro-2,2,4-trimethylquinoline (20 mg), cesium carbonate (63 mg), tetrabutylammonium bromide (29 mg) and chloromethylcyclopropane (8.4 l) in acetonitrile (1 ml) was stirred at 50° C. for 18 h. The reaction mixture was concentrated in vacuo and the residue was chromatographed on silicagel in heptane/ethyl acetate=1/0=>6/4 (v/v) as eluent.

Yield: 10 mg. MS-ESI: [M+H]$^+$=364.2; HPLC: R$_t$=10.73 min. (method 1)

Example 40

1-Acetyl-6-(3-pyridylmethyl)oxy-4-phenyl-1,2,3,4-tetrahydro-2,2,4-trimethylquinoline Alkylation of 1-acetyl-6-hydroxy-4-phenyl-1,2,3,4-tetrahydro-2,2,4-trimethylquinoline (20 mg) with 3-picolylchloride.HCl (12 mg), cesium carbonate (63 mg) and tetrabutylammonium bromide (30 mg) acetonitrile (1 ml) was performed according to the method described in example 39.

Yield: 10 mg: MS-ESI: [M+H]$^+$=401.2; HPLC: R$_t$=8.40 min. (method 1)

Example 41

1-Acetyl-6-ethyl-4-phenyl-1,2,3,4-tetrahydro-2,2,4-trimethylquinoline (a). 1,2-Dihydro-6-ethyl-2,2,4-trimethylquinoline Skraup reaction of p-ethylaniline (1.0 g) and iodine (0.34 g) in mesityl oxide (5 ml) was performed according to the method described in example 1.

Yield: 800 mg. MS-ESI: [M+H]$^+$=202.2

(b). 1-Acetyl-6-ethyl-1,2,3,4-tetrahydro-2,2,4-trimethylquinoline

Acylation of 1,2-dihydro-6-ethyl-2,2,4-trimethylquinoline (800 mg) with acetyl chloride (3.5 ml) and a catalytic amount of N,N-dimethylaminopyridine in pyridine (25 ml) was performed according to the method described in example 37.

Yield: 410 mg. MS-ESI: [M+H]$^+$=244.2

(c). 1-Acetyl-6-ethyl-4-phenyl-1,2,3,4-tetrahydro-2,2,4-trimethylquinoline

Friedel-Crafts alkylation of benzene (10 ml) with 1-acetyl-6-ethyl-1,2,3,4-tetrahydro-2,2,4-trimethylquinoline (410

33 mg) in the presence of AlCl$_3$ (710 mg) was performed according to the method described in example 3.
Yield: 407 mg. MS-ESI: [M+H]$^+$=322.4

Example 42

1-Acetyl-6-(1,1'-biphenyl)-4-phenyl-1,2,3,4-tetrahydro-2,2,4-trimethylquinoline (a). 1-Acetyl-6-iodo-4-phenyl-1,2,3,4-tetrahydro-2,2,4-trimethylquinoline A sodium nitrite solution (31 mg) was added dropwise to a cooled (0° C.) solution of 1-acetyl-6-amino-4-phenyl-1,2,3,4-tetrahydro-2,2,4-trimethylquinoline (128 mg) and sulfuric acid (82 mg) in water (2 ml). After stirring at 0° C. for 15 min, a potassium iodide solution (105 mg) was added. After stirring for 18 h, the reaction mixture was poured into dichloromethane. The organic layer was separated and washed with 5% aq. sodium thiosulfate and water, dried (MgSO$_4$) and concentrated in vacuo.
Yield: 160 mg. MS-ESI: [M+H]$^+$=420.0

(b). 1-Acetyl-6-(1,1'-biphenyl-yl)-4-phenyl-1,2,3,4-tetrahydro-2,2,4-trimethylquinoline Suzuki cross-coupling of 1-acetyl-6-iodo-4-phenyl-1,2,3,4-tetrahydro-2,2,4-trimethylquinoline (20 mg), (1,1'-biphenyl-4-yl)boronic acid (28 mg), cesium fluoride (15 mg), triphenylphosphine (5 mg) and tris(dibenzylideneacetone)dipalladium(0) (4.5 mg) in dimethoxyethane/ethanol 4:1 (v/v) (5 ml) was performed according to the method described in example 13.
Yield: 16 mg. MS-ESI: [M+H]$^+$=446.4; HPLC: R$_t$=6.84 min. (method 2)

Example 43

1-Acetyl-6-(4-chlorophenyl)-4-phenyl-1,2,3,4-tetrahydro-2,2,4-trimethylquinoline Suzuki cross-coupling of 1-acetyl-6-iodo-4-phenyl-1,2,3,4-tetrahydro-2,2,4-trimethylquinoline (20 mg), 4-chlorophenylboronic acid (22 mg), cesium fluoride (15 mg), triphenylphosphine (5 mg) and tris(dibenzylideneacetone) dipalladium(0) (4.5 mg) in dimethoxyethane/ethanol 4:1 (v/v) (5 ml) was performed according to the method described in example 13.
Yield: 8.6 mg. MS-ESI: [M+H]$^+$=404.4; HPLC: R$_t$=5.94 min. (method 2)

Example 44

1-Acetyl-6-amino-4-phenyl-1,2,3,4-tetrahydro-2,2,4,7-tetramethylquinoline (a). 1-Acetyl-6-amino-1,2-dihydro-2,2,4,7-tetramethylquinoline A mixture of N-Boc-2-methyl-1,4-phenylenediamine (2.3 g), magnesium sulfate (6.3 g), 4-tert-butylcatechol (100 mg) and iodine (300 mg) in acetone (15 ml) was stirred at reflux for 20 h. The reaction mixture was cooled to r.t. and filtered. The filtrate was concentrated in vacuo and the residue was chromatographed on SiO$_2$ with heptane/ethyl acetate=1/0=>3/1 (v/v) as eluent. The product, 6-(tert-butoxycarbonyl)amino-1,2-dihydro-2,2,4,7-tetramethylquinoline, was acylated with acetyl chloride (1.0 ml) in a mixture of pyridine (1.0 ml) and toluene (10 ml). After stirring for 1 h, the reaction mixture was washed with 3% aq. citric acid and water. The organic layer was dried (MgSO$_4$) and concentrated in vacuo. The residue was chromatographed on silicagel in heptane/ethyl acetate=1/0=>3/1 (v/v) as eluent.
Yield: 350 mg. MS-ESI: [M+H]$^+$=345.4

(b). 1-Acetyl-6-amino-4-phenyl-1,2,3,4-tetrahydro-2,2,4,7-tetramethylquinoline

AlCl$_3$ (266 mg) was added to a heated (70° C.) solution of 1-acetyl-6-amino-1,2-dihydro-2,2,4,7-tetramethylquinoline (100 mg) in benzene (10 ml). After 3 h, the mixture was cooled and concentrated in vacuo. The residue was dissolved in ethyl acetate and washed with water. The organic layer was separated, dried (MgSO$_4$) and concentrated in vacuo. The residue was chromatographed on silicagel in heptane/ethyl acetate=1/0=>3/1 (v/v) as eluent.
Yield: 75 mg. MS-ESI: [M+H]$^+$=323.4

Example 45

1-Acetyl-6-(4-phenylbenzoyl)amino-4-phenyl-1,2,3,4-tetrahydro-2,2,4,7-tetramethylquinoline Acylation of 1-acetyl-6-amino-4-phenyl-1,2,3,4-tetrahydro-2,2,4,7-tetramethylquinoline (20 mg) with 4-biphenylcarbonyl chloride (100 mg) and pyridine (100 l) in tetrahydrofuran (5 ml) was performed according to the method described in example 6.
Yield: 24 mg. MS-ESI: [M+H]$^+$=503.4

Example 46

1-Acetyl-6-(4-phenylbenzoyl)amino-8-methoxy-4-phenyl-1,2,3,4-tetrahydro-2,2,4-trimethylquinoline (a). 1-Acetyl-6-amino-8-methoxy-4-phenyl-1,2,3,4-tetrahydro-2,2,4-trimethylquinoline Skraup reaction of N-Boc-3-methoxy-1,4-phenylenediamine (450 mg), magnesium sulfate (1.0 g), 4-tert-butylcatachol (10 mg) and iodine (20 mg) in acetone (10 ml), acylation of the product with acetyl chloride (250 l) and pyridine (250 l) in toluene (10 ml) and subsequent Friedel-Crafts alkylation with AlCl$_3$ (266 mg) were performed according to the methods described in example 44.
Yield: 71 mg. MS-ESI: [M+H]$^+$=339.4

(b). 1-Acetyl-6-(4-phenylbenzoyl)amino-8-methoxy-4-phenyl-1,2,3,4-tetrahydro-2,2,4-trimethylquinoline Acylation of 1-acetyl-6-amino-8-methoxy-4-phenyl-1,2,3,4-tetrahydro-2,2,4-trimethylquinoline (20 mg) with 4-biphenylcarbonyl chloride (100 mg) and pyridine (100 l) in tetrahydrofuran (5 ml) was performed according to the method described in example 6.
Yield: 25 mg. MS-ESI: [M+H]$^+$=519.4

Example 47

1-Acetyl-6-(2-furoyl)amino-1,2,3,4-tetrahydro-4-toloyl-2,2,4-trimethylquinoline

Acylation of 1-acetyl-6-amino-4-toloyl-1,2,3,4-tetrahydro-2,2,4-trimethylquinoline (10 mg) with 2-furoyl chloride (8.1 mg) and N,N-diisopropylethylamine (20 l) in tetrahydrofuran (1 ml) was performed according to the method described in example 6.

Yield: 12 mg. MS-ESI: [M+H]$^+$=417.4; HPLC: R$_t$=4.90 min. (method 2)

Example 48

1-Acetyl-6-(4-phenylbenzoyl)amino-1,2,3,4-tetrahydro-4-toloyl-2,2,4-trimethylquinoline Acylation of 1-acetyl-6-amino-4-toloyl-1,2,3,4-tetrahydro-2,2,4-trimethylquinoline (10 mg) with 4-biphenylcarbonyl chloride (14 mg) and N,N-diisopropylethylamine (20 l) in tetrahydrofuran (1 ml) was performed according to the method described in example 6.

Yield: 9.3 mg. MS-ESI: [M+H]$^+$=503.4; HPLC: R$_t$=6.08 min. (method 2)

Example 49

1-Acetyl-6-(ethyl malonyl)amino-1,2,3,4-tetrahydro-4-toloyl-2,2,4-trimethylquinoline Acylation of 1-acetyl-6-amino-4-toloyl-1,2,3,4-tetrahydro-2,2,4-trimethylquinoline (10 mg) with ethyl malonyl chloride (9.4 mg) and N,N-diisopropylethylamine (20 l) in tetrahydrofuran (1 ml) was performed according to the method described in example 6.

Yield: 12 mg. MS-ESI: [M+H]$^+$=437.4; HPLC: R$_t$=4.71 min. (method 2)

Example 50

1-Acetyl-6-(3,5-dibromobenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 3,5-dibromobenzoic acid (10 mg) and N,N-diisopropylethylamine (22 l) in tetrahydrofuran (1 ml) was performed according to the method described in example 11.

Yield: 15.9 mg. MS-ESI: [M+H]$^+$=470.9; HPLC: R$_t$=10.11 min. (method 1)

Example 51

1-Acetyl-6-(5-bromo-2-methylaminobenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 5-bromo-2-methylaminobenzoic acid (8.4 mg) and N,N-diisopropylethylamine (22 l) in tetrahydrofuran (1 ml) was performed according to the method described in example 11.

Yield: 13.2 mg. MS-ESI: [M+H]$^+$=522.1; HPLC: R$_t$=8.95 min. (method 1)

Example 52

1-Acetyl-6-(3,4,5-trimethoxybenzoyl)amino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (10 mg) with 3,4,5-trimethoxybenzoyl chloride (12 mg) and N,N-diisopropylethylamine (22 l) in tetrahydrofuran (1 ml) was performed according to the method described in example 6.

Yield: 14.5 mg. MS-ESI: [M+H]$^+$=503.2; HPLC: R$_t$=11.26 min. (method 1)

Example 53

1-Acetyl-6-(3,5-dichloro-2,6-dimethoxybenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 3,5-dichloro-2,6-dimethoxybenzoic acid (9.0 mg) and N,N-diisopropylethylamine (22 l) in tetrahydrofuran (1 ml) was performed according to the method described in example 11.

Yield: 15.1 mg. MS-ESI: [M+H]$^+$=541.1; HPLC: R$_t$=10.92 min. (method 1)

Example 54

1-Acetyl-6-(2-acetyloxybenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 2-acetyloxybenzoic acid (6.0 mg) and N,N-diisopropylethylamine (22 l) in tetrahydrofuran (1 ml) was performed according to the method described in example 11.

Yield: 1.1 mg. MS-ESI: [M+H]$^+$=471.2; HPLC: R$_t$=14.35 min. (method 1)

Example 55

1-Acetyl-6-(2-acetamido-5-bromobenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 2-acetamido-5-bromobenzoic acid (6.0 mg) and N,N-diisopropylethylamine (22 l) in tetrahydrofuran (1 ml) was performed according to the method described in example 11.

Yield: 2.3 mg. MS-ESI: [M+H]$^+$=530.2; HPLC: R$_t$=12.01 min. (method 1)

Example 56

1-Acetyl-6-(5-bromo-2-N,N-dimethylcarbamoylbenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 5-bromosalicylic acid (8.0 mg) and N,N-diisopropylethylamine (22 l) in tetrahydrofuran (1 ml) was performed according to the method described in example 11.

Yield: 3.0 mg. MS-ESI: [M+H]$^+$=580.2; HPLC: R$_t$=12.53 min. (method 1)

Example 57

1-Acetyl-6-(2-[4-toloyloxy]benzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (10 mg) with 2-[4-toloyloxy]benzoic acid (8.0 mg) and N,N-diisopropylethylamine (22 l) in tetrahydrofuran (1 ml) was performed according to the method described in example 11.

Yield: 8.0 mg. MS-ESI: [M+H]$^+$=519.4; HPLC: R$_t$=13.11 min. (method 1)

Example 58

1-Acetyl-6-(2-methylsulfonyloxybenzoyl)amino-4-phenyl-1,2,3,4-tetrahydro-2,2,4-trimethylquinoline (a). 1-Acetyl-6-(2-methoxybenzoyl)amino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (0.60 g) with 2-methoxybenzoyl chloride (1.0 g) and N,N-diisopropylethylamine (1.7 ml) in tetrahydrofuran (60 ml) was performed according to the method described in example 6.

Yield: 0.65 g. MS-ESI: [M+H]$^+$=443.4

(b). 1-Acetyl-6-(2-hydroxybenzoyl)amino-4-phenyl-1,2,3,4-tetrahydro-2,2,4-trimethylquinoline BBr$_3$ (0.69 ml) was added dropwise to a solution of 1-acetyl-6-(2-methoxybenzoyl)amino-4-phenyl-1,2,3,4-tetrahydro-2,2,4-trimethylquinoline (0.64 g) in dichloromethane (40 mL). After stirring for 4 h, TLC indicated complete conversion. Water was added to the reaction mixture and stirring was continued for 15 min. The mixture was washed with 5% aq. NaHCO$_3$ and water. The organic layer was dried (MgSO$_4$) and concentrated in vacuo. The resulting product was used without further purification.

Yield: 0.62 g. MS-ESI: [M+H]$^+$=429.4

(c). 1-Acetyl-6-(2-methylsulfonyloxybenzoyl)amino-4-phenyl-1,2,3,4-tetrahydro-2,2,4-trimethylquinoline Sulfonylation of 1-acetyl-6-(2-hydroxybenzoyl)amino-4-phenyl-1,2,3,4-tetrahydro-2,2,4-trimethylquinoline (12 mg) with methylsulfonyl chloride (6.5 µl) was performed in pyridine (1 ml). TLC analysis after stirring for 16 h showed conversion to a higher-running product. The mixture was concentrated, the residue was dissolved in dichloromethane and washed with water. The organic layer was dried (Na$_2$SO$_4$) and concentrated in vacuo. The crude product was purified by silica gel column chromatography. Eluent: heptane/ethyl acetate=8/2 (v/v).

Yield: 8.0 mg. MS-ESI: [M+H]$^+$=507.4; HPLC: R$_t$=5.03 min. (method 2)

Example 59

1-Acetyl-6-(2-[3,5-dimethylisoxazole-4-sulfonyl]oxybenzoyl)amino-4-phenyl-1,2,3,4-tetrahydro-2,2,4-trimethylquinoline Sulfonylation of 1-acetyl-6-(2-hydroxybenzoyl)amino-4-phenyl-1,2,3,4-tetrahydro-2,2,4-trimethylquinoline (20 mg) with 3,5-dimethylisoxazole-4-sulfonyl chloride (27 mg) in pyridine (2 ml) was performed according to the method described in example 58.

Yield: 14 mg. MS-ESI: [M+H]$^+$=588.4; HPLC: R$_t$=14.46 min. (method 1)

Example 60

1-Acetyl-6-(2-methoxycarbonylethylcarbonyloxybenzoyl)amino-4-phenyl-1,2,3,4-tetrahydro-2,2,4-trimethylquinoline Acylation of 1-acetyl-6-(2-hydroxybenzoyl)amino-4-phenyl-1,2,3,4-tetrahydro-2,2,4-trimethylquinoline (20 mg) with 3-carbomethoxypropionyl chloride (14 mg) and N,N-diisopropylethylamine (40 µl) in tetrahydrofuran (2 ml) was performed according to the method described in example 6.

Yield: 21.4 mg. MS-ESI: [M+H]$^+$=543.6; HPLC: R$_t$=6.98 min. (method 1)

Example 61

1-Acetyl-6-(2-[5-methylisoxazole-3-carbonyl]oxybenzoyl)amino-4-phenyl-1,2,3,4-tetrahydro-2,2,4-trimethylquinoline Acylation of 1-acetyl-6-(2-hydroxybenzoyl)amino-4-phenyl-1,2,3,4-tetrahydro-2,2,4-trimethylquinoline (15 mg) with 5-methylisoxazole-3-carbonyl chloride (10 mg) and N,N-diisopropylethylamine (30 µl) in tetrahydrofuran (1 ml) was performed according to the method described in example 6.

Yield: 4.0 mg. MS-ESI: [M+H]$^+$=538.4; HPLC: R$_t$=9.84 min. (method 1)

Example 62

1-Acetyl-6-(2-[2-oxazolidinone-5-methyl]oxybenzoyl)amino-4-phenyl-1,2,3,4-tetrahydro-2,2,4-trimethylquinoline Alkylation of 1-acetyl-6-(2-hydroxybenzoyl)amino-4-phenyl-1,2,3,4-tetrahydro-2,2,4-trimethylquinoline (20 mg) with 5-chloromethyl-2-oxazolidinone (7 mg), cesium carbonate (63 mg) and tetrabutylammonium bromide (30 mg) in acetonitrile (1 ml) was performed according to the method described in example 39.

Yield: 25 mg. MS-ESI: [M+H]$^+$=542.4; HPLC: R$_t$=8.21 min. (method 1)

Example 63

1-Acetyl-6-(2-[morpholino-4-carbonyl]oxybenzoyl)amino-4-phenyl-1,2,3,4-tetrahydro-2,2,4-trimethylquinoline Acylation of 1-acetyl-6-(2-hydroxybenzoyl)amino-4-phenyl-1,2,3,4-tetrahydro-2,2,4-trimethylquinoline (15 mg) with morpholino-4-carbonyl chloride (12 µl) and N,N-diisopropylethylamine (30 µl) in tetrahydrofuran (1 ml) was performed according to the method described in example 6.

Yield: 5.4 mg. MS-ESI: [M+H]$^+$=542.4; HPLC: R$_t$=10.02 min. (method 1)

Example 64

1-Acetyl-6-(2-phenylaminobenzoyl)amino-4-phenyl-1,2,3,4-tetrahydro-2,2,4-trimethylquinoline HATU condensation of 1-acetyl-6-amino-4-phenyl-1,2,3,4-tetrahydro-2,2,4-trimethylquinoline (15 mg) with N-phenylanthranilic acid (21 mg) and N,N-diisopropylethylamine (33 l) in tetrahydrofuran (1 ml) was performed according to the method described in example 11.

Yield: 5.8 mg. MS-ESI: [M+H]$^+$=504.4; HPLC: R$_t$=13.42 min. (method 1)

Example 65

1-Acetyl-6-(2-pyrrolidone-N-ethylcarbonyl)amino-4-phenyl-1,2,3,4-tetrahydro-2,2,4-trimethylquinoline (a). 1-Acetyl-6-acryloylamino-4-phenyl-1,2,3,4-tetrahydro-2,2,4-trimethylquinoline Acylation of 1-acetyl-6-amino-4-phenyl-1,2,3,4-tetrahydro-2,2,4-trimethylquinoline (0.12 g) with acryloyl chloride (39 μl) and N,N-diisopropylethylamine (0.21 ml) in tetrahydrofuran (10 ml) was performed according to the method described in example 6.

Yield: 0.13 g. MS-ESI: [M+H]$^+$=363.2

(b). 1-Acetyl-6-(2-pyrrolidone-N-ethylcarbonyl)amino-4-phenyl-1,2,3,4-tetrahydro-2,2,4-trimethylquinoline To a mixture of 2-pyrrolidone (19 mg) and NaH (18 mg, 60% in oil) in THF (1 mL) was added 1-acetyl-6-acryloylamino-4-phenyl-1,2,3,4-tetrahydro-2,2,4-trimethylquinoline (8 mg) in THF (1 mL). After stirring for 18 h, TLC analysis indicated conversion into a higher-running product. The mixture was diluted with ethyl acetate and washed with water, 0.5 N HCl and water. The organic layer was dried (Na$_2$SO$_4$) and concentrated in vacuo. Purification was accomplished by silica gel column chromatography, using heptane/ethyl acetate=8/2⇒1/1 (v/v) as eluent.

Yield: 4.6 mg. MS-ESI: [M+H]$^+$=448.4; HPLC: R$_t$=4.51 min. (method 2)

Example 66

1-Acetyl-6-(ethoxyethoxyethylcarbonyl)amino-4-phenyl-1,2,3,4-tetrahydro-2,2,4-trimethylquinoline Michael addition of 2-ethoxyethanol (19 mg) and 1-acetyl-6-acryloylamino-4-phenyl-1,2,3,4-tetrahydro-2,2,4-trimethylquinoline (8 mg) in THF (1 mL) was performed according to the method described in example 65.

Yield: 1.0 mg. MS-ESI: [M+H]$^+$=453.4; HPLC: R$_t$=5.03 min. (method 2)

Example 67

1-Acetyl-6-(2-pyrrolidone-N-methoxycarbonylmethylcarbonyl)amino-4-phenyl-1,2,3,4-tetrahydro-2,2,4-trimethylquinoline Condensation of N-hydroxymethyl-2-pyrrolidone (22 mg) and 1-acetyl-6-(hydroxycarbonylmethylcarbonyl)amino-4-phenyl-1,2,3,4-tetrahydro-2,2,4-trimethylquinoline (15 mg) under the agency of HATU (29 mg) and N,N-diisopropylethylamine (33 l) in tetrahydrofuran (2 ml) was performed according to the method described in example 11.

Yield: 4.6 mg. MS-ESI: [M+H]$^+$=478.4; HPLC: R$_t$=5.53 min. (method 2)

Example 68

1-Acetyl-6-(tert-butylcarbamoyl-N-[2-ethoxy]carbonylmethylcarbonyl)amino-4-phenyl-1,2,3,4-tetrahydro-2,2,4-trimethylquinoline Condensation of tert-butyl-N-(2-hydroxyethyl)carbamate (29 μl) and 1-acetyl-6-(hydroxycarbonylmethylcarbonyl)amino-4-phenyl-1,2,3,4-tetrahydro-2,2,4-trimethylquinoline (15 mg) under the agency of HATU (29 mg) and N,N-diisopropylethylamine (33 l) in tetrahydrofuran (2 ml) was performed according to the method described in example 11.

Yield: 11 mg. MS-ESI: [M+H]$^+$=538.4; HPLC: R$_t$=5.32 min. (method 2)

Example 69

1-Acetyl-6-(2-furylmethoxycarbonylmethylcarbonyl)amino-4-phenyl-1,2,3,4-tetrahydro-2,2,4-trimethylquinoline Condensation of furfuryl alcohol (17 μl) and 1-acetyl-6-(hydroxycarbonylmethylcarbonyl)amino-4-phenyl-1,2,3,4-tetrahydro-2,2,4-trimethylquinoline (15 mg) under the agency of HATU (29 mg) and N,N-diisopropylethylamine (33 l) in tetrahydrofuran (2 ml) was performed according to the method described in example 11.

Yield: 7.1 mg. MS-ESI: [M+H]$^+$=475.4; HPLC: R$_t$=5.30 min. (method 2)

Example 70

1-Acetyl-6-([cyclopropylmethylaminomethylcarbonyl)amino-4-phenyl-1,2,3,4-tetrahydro-2,2,4-trimethylquinoline Alkylation of cyclopropylmethylamine (4 l) with 1-acetyl-6-(bromoacetyl)amino-4-phenyl-1,2,3,4-tetrahydro-2,2,4-trimethylquinoline (10 mg) and N,N-diisopropylethylamine (13 l) in dichloromethane (1 ml) was performed according to the method described in example 29.

Yield: 6.8 mg. MS-ESI: [M+H]$^+$=535.6; HPLC: R$_t$=6.29 min. (method 2)

Example 71

1-Acetyl-4-(2-methoxyphenyl)-6-(4-phenylbenzoyl)amino-1,2,3,4-tetrahydro-2,2,4-trimethylquinoline (a). 1-Acetyl-6-(4-phenylbenzoyl)amino-1,2-dihydro-2,2,4-trimethylquinoline 1-Acetyl-6-(tert-butoxycarbonyl)amino-1,2-dihydro-2,2,4-trimethylquinoline (1.0 g) was dissolved in a mixture of trifluoroacetic acid/CH$_2$Cl$_2$ (1/1, v/v, 25 ml) and stirred for 2 h. The reaction mixture was concentrated in vacuo, diluted with ethyl acetate and washed with 5% aq. NaHCO$_3$. The organic layer was separated, dried (MgSO$_4$) and concentrated. The residue was dissolved in CH$_2$Cl$_2$ (25 ml), N,N-diisopropylethylamine (5.2 ml) and 4-phenylbenzoyl chloride (2.0 g) were added and the mixture was stirred for 16 h. The mixture was concentrated and chromatographed on silicagel in heptane/ethyl acetate=1/0⇒0/1 (v/v) as eluent.

Yield: 0.63 g. MS-ESI: [M+H]$^+$=411.2

(b). 1-Acetyl-4-(2-methoxyphenyl)-6-(4-phenylben-zoyl)amino-1,2,3,4-tetrahydro-2,2,4-trimethylquinoline and 1-acetyl-4-(4-methoxyphenyl)-6-(4-phenylbenzoyl)amino-1,2,3,4-tetrahydro-2,2,4-trimethylquinoline Friedel-Crafts alkylation of anisole (25 ml, stored on molecular sieves 3 Å) with 1-acetyl-6-(4-phenylbenzoyl) amino-1,2-dihydro-2,2,4-trimethylquinoline (0.50 g) in the presence of $AlCl_3$ (0.50 g) was performed according to the method described in example 3. Purification by silica gel chromatography (eluent: heptane/ethyl acetate=1/0⇒0/1, v,v) yielded the 2-methoxyphenyl-substituted derivative as minor product and the 4-methoxyphenyl-substituted derivative as the major product.

Yield: 46 mg. MS-ESI: $[M+H]^+$=518.0 (2-methoxyphenyl)

Yield: 0.20 g. MS-ESI: $[M+H]^+$=518.1 (4-methoxyphenyl)

Example 72

1-Acetyl-4-(4-hydroxyphenyl)-6-(4-phenylbenzoyl)amino-1,2,3,4-tetrahydro-2,2,4-trimethylquinoline To a cooled (0° C.) solution of 1-acetyl-4-(4-methoxyphenyl)-6-(4-phenylbenzoyl)amino-1,2,3,4-tetrahydro-2,2,4-trimethylquinoline (0.46 g) in $CH_2Cl_2$ was added $BBr_3$ under a nitrogen atmosphere. Complete conversion was reached after stirring for 3 h at room temperature. The mixture was cooled, 1 M NaOH was added until basic pH, subsequently ethyl acetate was added and the mixture was acidified with 1 M HCl. The organic layer was separated, dried ($MgSO_4$) and concentrated. The residue was chromatographed on silicagel in heptane/ethyl acetate=1/0⇒0/1 (v/v) as eluent.

Yield: 0.13 g. MS-ESI: $[M+H]^+$=504.0

Example 73

1-Acetyl-6-(5-methylnicotinoyl)amino-4-phenyl-1,2,3,4-tetrahydro-2,2,4-trimethylquinoline Condensation of 1-acetyl-6-amino-4-phenyl-1,2,3,4-tetrahydro-2,2,4-trimethylquinoline (0.10 g) with 5-methyl nicotinic acid (0.13 g) under the agency of HATU (0.18 g) and N,N-diisopropylethylamine (0.28 ml) in dichloromethane (2 ml) was performed according to the method described in example 11.

Yield: 0.12 g. MS-ESI: $[M+H]^+$=427.0

Example 74

CHO-FSH In Vitro Bio Activity

FSH activity of compounds were tested in Chinese Hamster Ovary (CHO) cells stably transfected with the human FSH receptor and cotransfected with a cAMP responsive element (CRE)/promotor directing the expression of a firefly luciferase reporter gene. Binding of ligand to the Gs-coupled FSH receptor will result in an increase of cAMP, which in turn will induce an increased transactivation of the luciferase reporter construct. The luciferase signal was quantified using a luminescence counter. For test compounds, $EC_{50}$ values (concentration of test compound causing half-maximal (50%) stimulation) were calculated. For that purpose the software program GraphPad PRISM, version 3.0 (GraphPad software Inc., San Diego) was used.

Compounds of all examples had an activity ($EC_{50}$) of less than $10^{-5}$M. The compounds of examples 1, 6-13, 15, 16, 21-24, 30, 36, 37, 45, 46, 48, 50-53, 55, 57, 58, 61, 63 and 64 showed an $EC_{50}$ of less than $10^{-7}$ M.

The invention claimed is:

1. A tetrahydroquinoline compound of Formula I,

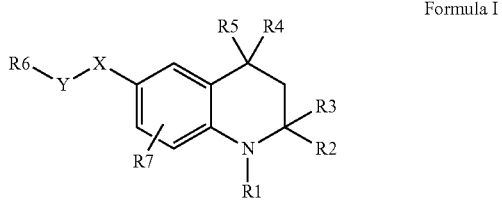

Formula I or a pharmaceutically acceptable salt thereof, wherein
$R^1$ is (1-6C)alkylcarbonyl;
$R^2$ and $R^3$ are (1-4C)alkyl;
$R^4$ is phenyl, optionally substituted with one or more substituents selected from the group hydroxy, halogen, (1-4C)alkyl, and (1-4C)alkoxy;
$R^5$ is (1-4C)alkyl;
Y—X is C(O)—O, C(O)—NH, or OC(O)—NH;
$R^6$ is (1-6C)alkyl, 1- or 2-adamantyl(1-4C)alkyl, heteroaryl selected from imidazolyl, thiadiazolyl, pyridyl, (benz)thienyl, (benzo)furyl, quinolyl, tetrahydroquinolyl, quinoxalyl, indolyl, thienyl and furyl, phenyl (1-4C)alkyl, (1-4C)alkyl heteroaryl, wherein the heteroaryl is selected from imidazolyl, thiadiazolyl, pyridyl, (benz)thienyl, (benzo)furyl, quinolyl, tetrahydroquinolyl, quinoxalyl, indolyl, thienyl and furyl, heterocycloalkyl(1-4C)alkyl, wherein the heterocycloalkyl is selected from piperidine, morpholine and pyrrolidine, $R^8,R^9$-aminocarbonyl(1-4C)alkyl, $R^8,R^9$-amino(1-4C) alkyl, $R^8$-oxycarbonyl(1-4C)alkyl, $R^8$-oxy(1-4C)alkyl or phenyl, wherein phenyl is optionally substituted with nitro, trifluoromethyl, chlorophenyl, pyridyl, morpholinocarbonyloxy, isoxazolecarbonyloxy, oxazolidinoneoxycarbonyl, (1-4C)alkoxycarbonyl(1-4C)alkylcarbonyloxy, (1-4C)alkylsulfonyloxy, dimethylisoxazolesulfonyloxy, and (di)phenylamino, or one or more of halogens, (1-4C)alkyl, (1-4C)alkoxy, (1-4C)(di)alkylamino, phenyl, and (1-4C)(di)alkylcarbamoyl;
$R^7$ is H, (1-4C)alkyl, or (1-4C)alkoxy;
$R^8$ is (1-4C)alkyl, phenyl(1-4C)alkyl, heteroaryl(1-4C) alkyl, wherein the heteroaryl is selected from imidazolyl, thiadiazolyl, pyridyl, (benz)thienyl, (benzo)furyl, quinolyl, tetrahydroquinolyl, quinoxalyl, indolyl, thienyl and furyl, (3-6C)cycloalkyl(1-4C)alkyl, heterocycloalkyl(1-4C)alkyl, wherein the heterocycloalkyl is selected from piperidine, morpholine and pyrrolidine, (1-4C)alkoxy(1-4C)alkyl, (1-4C)alkoxycarbonyl(1-4C) alkyl, t-butylcarbamoyl, benzyl optionally substituted with (1-4C)alkoxy or one or more halogens, or $R^8$ together with $R^9$ may form a heterocycloalkyl selected from azetidine, pyrrolidine, piperidine, piperazine, thiomorpholine and morpholine, wherein the heterocycloalkyl ring is optionally substituted with phenyl, and
$R^9$ is H, or (1-4C)alkyl,
wherein the compound is not 1-acetyl-6-benzoylamino-4-(4-methylphenyl)-1,2,3,4-tetrahydro-2,2,4-trimethylquinoline.

2. The tetrahydroquinoline compound of claim 1, wherein the tetrahydroquinoline compound of formula I, Y—X is C(O)—NH.

3. The tetrahydroquinoline compound of claim 1, wherein $R^6$ is heteroaryl selected from imidazolyl, thiadiazolyl, pyridyl, (benz)thienyl, (benzo)furyl, quinolyl, tetrahydroquinolyl, quinoxalyl, indolyl, thienyl and furyl, phenyl(1-4C)alkyl, (1-4C)alkylheteroaryl, wherein the heteroaryl is selected from imidazolyl, thiadiazolyl, pyridyl, (benz)thienyl, (benzo)furyl, quinolyl, tetrahydroquinolyl, quinoxalyl, indolyl, thienyl and furyl, or phenyl optionally substituted with nitro, trifluoromethyl, chlorophenyl, pyridyl, morpholinocarbonyloxy, isoxazolecarbonyloxy, oxazolidinoneoxycarbonyl, (1-4C)alkoxycarbonyl(1-4C)alkylcarbonyloxy, (1-4C)alkylsulfonyloxy, (1-4C)alkylsulfonyloxy, dimethylisoxazolesulfonyloxy, or (di)phenylamino, or one or more of halogens, (1-4C)alkyl, (1-4C)alkoxy, (1-4C)(di)alkylamino, phenyl, and (1-4C)(di)alkylcarbamoyl.

* * * * *